(12) United States Patent
Krivoruchko

(10) Patent No.: US 12,109,113 B2
(45) Date of Patent: *Oct. 8, 2024

(54) PROSTHETIC HEART VALVE DEVICES WITH TETHERED ANCHORS AND ASSOCIATED SYSTEMS AND METHODS

(71) Applicant: Medtronic Vascular, Inc., Santa Rosa, CA (US)

(72) Inventor: Mike Krivoruchko, Forestville, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 579 days.

This patent is subject to a terminal disclaimer.

(21) Appl. No.: 17/323,481

(22) Filed: May 18, 2021

(65) Prior Publication Data

US 2021/0267760 A1 Sep. 2, 2021

Related U.S. Application Data

(63) Continuation of application No. 16/293,557, filed on Mar. 5, 2019, now Pat. No. 11,033,390, which is a
(Continued)

(51) Int. Cl.
*A61F 2/24* (2006.01)
*A61B 17/04* (2006.01)

(52) U.S. Cl.
CPC ........ *A61F 2/2457* (2013.01); *A61B 17/0401* (2013.01); *A61F 2/2418* (2013.01);
(Continued)

(58) Field of Classification Search
CPC .... A61F 2/2418; A61F 2/2457; A61F 2/2451; A61F 2/2481; A61B 17/0057;
(Continued)

(56) References Cited

U.S. PATENT DOCUMENTS 3,526,219 A 9/1970 Balamuth
3,565,062 A 2/1971 Kuris
(Continued)

FOREIGN PATENT DOCUMENTS

CN 440261 9/2003
CN 101076290 11/2007
(Continued)

OTHER PUBLICATIONS

US 9,265,606 B2, 02/2016, Buchbinder et al. (withdrawn)
(Continued)

*Primary Examiner* — Alvin J Stewart
(74) *Attorney, Agent, or Firm* — Medler Ferro Woodhouse & Mills PLLC

(57) ABSTRACT

Prosthetic heart valve devices with tethered anchors and associated systems and methods are disclosed herein. A heart valve device configured in accordance with embodiments of the present technology can include, for example, a valve support for carrying a prosthetic valve. The valve support can be configured to be implanted at an annulus of a native mitral valve. The device can further include at least one elongated flexible member extending from the valve support in a ventricular direction, and an anchor coupled to the valve support via the elongated flexible member. The anchor can be shaped to wrap around an exterior area of an apical portion of the heart. In addition, the anchor can inhibit retrograde migration of the valve support.

22 Claims, 7 Drawing Sheets

Related U.S. Application Data continuation of application No. 15/489,889, filed on Apr. 18, 2017, now Pat. No. 10,265,172.

(60) Provisional application No. 62/329,400, filed on Apr. 29, 2016.

(52) U.S. Cl.
CPC .... *A61F 2/2427* (2013.01); *A61B 2017/0417* (2013.01); *A61F 2/2481* (2013.01); *A61F 2210/0014* (2013.01); *A61F 2220/0008* (2013.01)

(58) Field of Classification Search
CPC .. A61B 2017/00243; A61B 2017/0406; A61B 2017/0448
See application file for complete search history.

(56) References Cited

U.S. PATENT DOCUMENTS

| | | |
|---|---|---|
| 3,589,363 A | 6/1971 | Banko et al. |
| 3,667,474 A | 6/1972 | Lapkin et al. |
| 3,823,717 A | 7/1974 | Pohlman et al. |
| 3,861,391 A | 1/1975 | Antonevich et al. |
| 3,896,811 A | 7/1975 | Storz |
| 4,042,979 A | 8/1977 | Angell |
| 4,188,952 A | 2/1980 | Loschilov et al. |
| 4,431,006 A | 2/1984 | Trimmer et al. |
| 4,445,509 A | 5/1984 | Auth |
| 4,484,579 A | 11/1984 | Meno et al. |
| 4,490,859 A | 1/1985 | Black et al. |
| 4,587,958 A | 5/1986 | Noguchi et al. |
| 4,589,419 A | 5/1986 | Laughlin et al. |
| 4,602,911 A | 7/1986 | Ahmadi et al. |
| 4,646,736 A | 3/1987 | Auth |
| 4,692,139 A | 9/1987 | Stiles |
| 4,747,821 A | 5/1988 | Kensey et al. |
| 4,750,902 A | 6/1988 | Wuchinich et al. |
| 4,777,951 A | 10/1988 | Cribier et al. |
| 4,787,388 A | 11/1988 | Hofmann |
| 4,796,629 A | 1/1989 | Grayzel |
| 4,808,153 A | 2/1989 | Parisi |
| 4,819,751 A | 4/1989 | Shimada et al. |
| 4,841,977 A | 6/1989 | Griffith et al. |
| 4,870,953 A | 10/1989 | DonMicheal et al. |
| 4,878,495 A | 11/1989 | Grayzel |
| 4,898,575 A | 2/1990 | Fischell et al. |
| 4,909,252 A | 3/1990 | Goldberger |
| 4,919,133 A | 4/1990 | Chiang |
| 4,920,954 A | 5/1990 | Alliger et al. |
| 4,936,281 A | 6/1990 | Stasz |
| 4,960,411 A | 10/1990 | Buchbinder |
| 4,960,424 A * | 10/1990 | Grooters ............... A61F 2/2457 128/898 |
| 4,986,830 A | 1/1991 | Owens et al. |
| 4,990,134 A | 2/1991 | Auth |
| 5,058,570 A | 10/1991 | Idemoto et al. |
| 5,069,664 A | 12/1991 | Guess et al. |
| 5,076,276 A | 12/1991 | Sakurai et al. |
| 5,106,302 A | 4/1992 | Farzin-Nia et al. |
| 5,248,296 A | 9/1993 | Alliger |
| 5,267,954 A | 12/1993 | Nita |
| 5,269,291 A | 12/1993 | Carter |
| 5,295,958 A | 3/1994 | Shturman |
| 5,304,115 A | 4/1994 | Pflueger et al. |
| 5,314,407 A | 5/1994 | Auth et al. |
| 5,318,014 A | 6/1994 | Carter |
| 5,332,402 A | 7/1994 | Teitelbaum |
| 5,344,426 A | 9/1994 | Lau et al. |
| 5,344,442 A | 9/1994 | Deac |
| 5,352,199 A | 10/1994 | Tower |
| 5,356,418 A | 10/1994 | Shturman |
| 5,397,293 A | 3/1995 | Alliger et al. |
| 5,411,552 A | 5/1995 | Andersen et al. |
| 5,443,446 A | 8/1995 | Shturman |
| 5,449,373 A | 9/1995 | Pinchasik et al. |
| 5,489,297 A | 2/1996 | Duran |
| 5,584,879 A | 12/1996 | Reimold et al. |
| 5,609,151 A | 3/1997 | Mulier et al. |
| 5,626,603 A | 5/1997 | Venturelli et al. |
| 5,656,036 A | 8/1997 | Palmaz |
| 5,662,671 A | 9/1997 | Barbut et al. |
| 5,662,704 A | 9/1997 | Gross et al. |
| 5,681,336 A | 10/1997 | Clement et al. |
| 5,695,507 A | 12/1997 | Auth et al. |
| 5,725,494 A | 3/1998 | Brisken |
| 5,782,931 A | 7/1998 | Yang et al. |
| 5,817,101 A | 10/1998 | Fiedler |
| 5,827,229 A | 10/1998 | Auth et al. |
| 5,827,321 A | 10/1998 | Roubin et al. |
| 5,840,081 A | 11/1998 | Andersen et al. |
| 5,853,422 A | 12/1998 | Huebsch et al. |
| 5,855,601 A | 1/1999 | Bessler et al. |
| 5,868,781 A | 2/1999 | Killion |
| 5,873,811 A | 2/1999 | Wang et al. |
| 5,904,679 A | 5/1999 | Clayman |
| 5,957,882 A | 9/1999 | Nita et al. |
| 5,972,004 A | 10/1999 | Williamson, IV et al. |
| 5,989,208 A | 11/1999 | Nita |
| 5,989,280 A | 11/1999 | Euteneuer et al. |
| 6,047,700 A | 4/2000 | Eggers et al. |
| 6,056,759 A | 5/2000 | Fiedler |
| 6,085,754 A * | 7/2000 | Alferness ............... D04B 21/12 623/66.1 |
| 6,113,608 A | 9/2000 | Monroe et al. |
| RE36,939 E | 10/2000 | Tachibana et al. |
| 6,129,734 A | 10/2000 | Shturman et al. |
| 6,132,444 A | 10/2000 | Shturman et al. |
| 6,168,579 B1 | 1/2001 | Tsugita |
| 6,217,595 B1 | 4/2001 | Shturman et al. |
| 6,254,635 B1 | 7/2001 | Schroeder et al. |
| 6,295,712 B1 | 10/2001 | Shturman et al. |
| 6,306,414 B1 | 10/2001 | Koike |
| 6,321,109 B2 | 11/2001 | Ben-Haim et al. |
| 6,332,893 B1 * | 12/2001 | Mortier ................. A61F 2/2487 623/2.41 |
| 6,402,679 B1 | 6/2002 | Mortier et al. |
| 6,423,032 B2 | 7/2002 | Parodi |
| 6,425,916 B1 | 7/2002 | Garrison et al. |
| 6,440,164 B1 | 8/2002 | DiMatteo et al. |
| 6,454,737 B1 | 9/2002 | Nita et al. |
| 6,454,757 B1 | 9/2002 | Nita et al. |
| 6,454,799 B1 | 9/2002 | Schreck |
| 6,458,153 B1 | 10/2002 | Bailey et al. |
| 6,461,382 B1 | 10/2002 | Cao |
| 6,494,890 B1 | 12/2002 | Shturman et al. |
| 6,494,891 B1 | 12/2002 | Cornish et al. |
| 6,505,080 B1 | 1/2003 | Sutton |
| 6,530,952 B2 | 3/2003 | Vesely |
| 6,540,782 B1 | 4/2003 | Snyders |
| 6,562,067 B2 | 5/2003 | Mathis |
| 6,565,588 B1 | 5/2003 | Clement et al. |
| 6,569,196 B1 | 5/2003 | Vesely |
| 6,579,308 B1 | 6/2003 | Jansen et al. |
| 6,582,462 B1 | 6/2003 | Andersen et al. |
| 6,595,912 B2 | 7/2003 | Lau et al. |
| 6,605,109 B2 | 8/2003 | Fiedler |
| 6,616,689 B1 | 9/2003 | Ainsworth et al. |
| 6,623,452 B2 | 9/2003 | Chien et al. |
| 6,638,288 B1 | 10/2003 | Shturman et al. |
| 6,648,854 B1 | 11/2003 | Patterson et al. |
| 6,689,086 B1 | 2/2004 | Nita et al. |
| 6,702,748 B1 | 3/2004 | Nita et al. |
| 6,730,121 B2 | 5/2004 | Ortiz et al. |
| 6,746,463 B1 | 6/2004 | Schwartz |
| 6,811,801 B2 | 11/2004 | Nguyen et al. |
| 6,818,001 B2 | 11/2004 | Wulfman et al. |
| 6,843,797 B2 | 1/2005 | Nash et al. |
| 6,852,118 B2 | 2/2005 | Shturman et al. |
| 6,855,123 B2 | 2/2005 | Nita |
| 6,869,439 B2 | 3/2005 | White et al. |
| 6,951,571 B1 | 10/2005 | Srivastava |
| 6,986,775 B2 | 1/2006 | Morales et al. |

(56) References Cited

U.S. PATENT DOCUMENTS

| | | |
|---|---|---|
| 7,018,404 B2 | 3/2006 | Holmberg et al. |
| 7,052,487 B2 | 5/2006 | Cohn et al. |
| 7,060,021 B1 | 6/2006 | Wilk |
| 7,077,861 B2 | 7/2006 | Spence |
| 7,125,420 B2 | 10/2006 | Rourke et al. |
| 7,186,264 B2 | 3/2007 | Liddicoat et al. |
| 7,261,732 B2 | 8/2007 | Justino |
| 7,296,577 B2 | 11/2007 | Lashinski et al. |
| 7,381,218 B2 | 6/2008 | Schreck |
| 7,404,824 B1 | 7/2008 | Webler et al. |
| 7,442,204 B2 | 10/2008 | Schwammenthal et al. |
| 7,473,275 B2 | 1/2009 | Marquez |
| 7,510,575 B2 | 3/2009 | Spenser et al. |
| 7,585,321 B2 | 9/2009 | Cribier |
| 7,588,582 B2 | 9/2009 | Starksen et al. |
| 7,621,948 B2 | 11/2009 | Herrmann et al. |
| 7,708,775 B2 | 5/2010 | Rowe et al. |
| 7,748,389 B2 | 7/2010 | Salahieh et al. |
| 7,753,922 B2 | 7/2010 | Starksen |
| 7,753,949 B2 | 7/2010 | Lamphere et al. |
| 7,803,168 B2 | 9/2010 | Gifford et al. |
| 7,857,845 B2 | 12/2010 | Stacchino et al. |
| 7,896,915 B2 | 3/2011 | Guyenot et al. |
| 7,942,928 B2 | 5/2011 | Webler et al. |
| 8,002,826 B2 | 8/2011 | Seguin |
| 8,052,750 B2 | 11/2011 | Tuval et al. |
| 8,062,355 B2 | 11/2011 | Figulla et al. |
| 8,109,996 B2 | 2/2012 | Stacchino et al. |
| 8,114,154 B2 | 2/2012 | Righini et al. |
| 8,226,711 B2 | 7/2012 | Mortier et al. |
| 8,252,051 B2 | 8/2012 | Chau et al. |
| 8,398,704 B2 | 3/2013 | Straubinger et al. |
| 8,403,981 B2 | 3/2013 | Forster et al. |
| 8,403,983 B2 | 3/2013 | Quadri et al. |
| 8,414,643 B2 | 4/2013 | Tuval et al. |
| 8,449,599 B2 | 5/2013 | Chau et al. |
| 8,496,671 B1 | 7/2013 | Hausen |
| 8,512,252 B2 | 8/2013 | Ludomirsky et al. |
| 8,518,107 B2 | 8/2013 | Tsukashima et al. |
| 8,523,883 B2 | 9/2013 | Saadat |
| 8,532,352 B2 | 9/2013 | Ionasec et al. |
| 8,540,767 B2 | 9/2013 | Zhang |
| 8,545,551 B2 | 10/2013 | Loulmet |
| 8,551,161 B2 | 10/2013 | Dolan |
| 8,579,788 B2 | 11/2013 | Orejola |
| 8,579,964 B2 | 11/2013 | Lane et al. |
| 8,585,755 B2 | 11/2013 | Chau et al. |
| 8,597,347 B2 | 12/2013 | Maurer et al. |
| 8,597,348 B2 | 12/2013 | Rowe et al. |
| 8,608,796 B2 | 12/2013 | Matheny |
| 8,608,797 B2 * | 12/2013 | Gross .............. A61F 2/2442 623/2.37 |
| 8,623,077 B2 | 1/2014 | Cohn |
| 8,628,566 B2 | 1/2014 | Eberhardt et al. |
| 8,632,585 B2 | 1/2014 | Seguin et al. |
| 8,632,586 B2 | 1/2014 | Spenser et al. |
| 8,634,935 B2 | 1/2014 | Gaudiani |
| 8,647,254 B2 | 2/2014 | Callas et al. |
| 8,652,203 B2 | 2/2014 | Quadri et al. |
| 8,652,204 B2 | 2/2014 | Quill et al. |
| 8,657,872 B2 | 2/2014 | Seguin |
| 8,672,998 B2 | 3/2014 | Lichtenstein et al. |
| 8,673,001 B2 | 3/2014 | Cartledge et al. |
| 8,679,176 B2 | 3/2014 | Matheny |
| 8,685,086 B2 | 4/2014 | Navia et al. |
| 8,688,234 B2 | 4/2014 | Zhu et al. |
| 8,690,858 B2 * | 4/2014 | Machold .......... A61B 17/0057 604/533 |
| 8,709,074 B2 | 4/2014 | Solem et al. |
| 8,712,133 B2 | 4/2014 | Guhring et al. |
| 8,715,160 B2 | 5/2014 | Raman et al. |
| 8,721,665 B2 | 5/2014 | Oz et al. |
| 8,721,718 B2 | 5/2014 | Kassab |
| 8,740,918 B2 | 6/2014 | Seguin |
| 8,747,460 B2 | 6/2014 | Tuval et al. |
| 8,758,431 B2 | 6/2014 | Orlov et al. |
| 8,758,432 B2 | 6/2014 | Solem |
| 8,771,292 B2 | 7/2014 | Allen et al. |
| 8,771,345 B2 | 7/2014 | Tuval et al. |
| 8,771,346 B2 | 7/2014 | Tuval et al. |
| 8,777,991 B2 | 7/2014 | Zarbatany et al. |
| 8,778,016 B2 | 7/2014 | Janovsky et al. |
| 8,781,580 B2 | 7/2014 | Hedberg et al. |
| 8,784,482 B2 | 7/2014 | Rahdert et al. |
| 8,792,699 B2 | 7/2014 | Guetter et al. |
| 8,795,356 B2 | 8/2014 | Quadri et al. |
| 8,801,779 B2 | 8/2014 | Seguin et al. |
| 8,808,356 B2 | 8/2014 | Braido et al. |
| 8,808,366 B2 | 8/2014 | Braido et al. |
| 8,812,431 B2 | 8/2014 | Voigt et al. |
| 8,828,043 B2 | 9/2014 | Chambers |
| 8,845,717 B2 | 9/2014 | Khairkhahan et al. |
| 8,845,723 B2 | 9/2014 | Spence et al. |
| 8,852,213 B2 | 10/2014 | Gammie et al. |
| 8,852,272 B2 | 10/2014 | Gross et al. |
| 8,858,622 B2 | 10/2014 | Machold et al. |
| 8,859,724 B2 | 10/2014 | Meier et al. |
| 8,864,822 B2 | 10/2014 | Spence et al. |
| 8,870,936 B2 | 10/2014 | Rowe |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,894,702 B2 | 11/2014 | Quadri et al. |
| 8,900,295 B2 | 12/2014 | Migliazza et al. |
| 8,926,694 B2 | 1/2015 | Costello |
| 8,932,348 B2 | 1/2015 | Solem et al. |
| 8,951,285 B2 | 2/2015 | Sugimoto et al. |
| 8,961,597 B2 | 2/2015 | Subramanian et al. |
| 8,968,393 B2 | 3/2015 | Rothstein |
| 8,968,395 B2 * | 3/2015 | Hauser ............ A61F 2/2466 623/2.36 |
| 8,974,445 B2 | 3/2015 | Warnking et al. |
| 8,979,922 B2 | 3/2015 | Jayasinghe et al. |
| 8,979,923 B2 | 3/2015 | Spence et al. |
| 8,986,370 B2 | 3/2015 | Annest |
| 8,986,376 B2 | 3/2015 | Solem |
| 8,992,604 B2 | 3/2015 | Gross et al. |
| 9,011,522 B2 | 4/2015 | Annest |
| 9,011,523 B2 | 4/2015 | Seguin |
| 9,017,399 B2 | 4/2015 | Gross et al. |
| 9,023,098 B2 | 5/2015 | Kuehn |
| 9,023,100 B2 | 5/2015 | Quadri et al. |
| 9,050,188 B2 | 6/2015 | Schweich, Jr. et al. |
| 9,066,800 B2 | 6/2015 | Clague et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,119,713 B2 | 9/2015 | Board et al. |
| 9,125,742 B2 | 9/2015 | Yoganathan et al. |
| 9,132,009 B2 | 9/2015 | Hacohen et al. |
| 9,138,312 B2 | 9/2015 | Tuval et al. |
| 9,138,313 B2 | 9/2015 | McGuckin, Jr. et al. |
| 9,180,005 B1 | 11/2015 | Lashinski et al. |
| 9,192,466 B2 | 11/2015 | Kovalsky et al. |
| 9,192,471 B2 | 11/2015 | Bolling |
| 9,198,756 B2 * | 12/2015 | Aklog .............. A61F 2/2451 |
| 9,232,942 B2 | 1/2016 | Seguin et al. |
| 9,232,999 B2 | 1/2016 | Maurer et al. |
| 9,241,790 B2 | 1/2016 | Lane et al. |
| 9,248,014 B2 | 2/2016 | Lane et al. |
| 9,254,192 B2 | 2/2016 | Lutter et al. |
| 9,271,833 B2 | 3/2016 | Kim et al. |
| 9,289,291 B2 | 3/2016 | Gorman, III et al. |
| 9,289,297 B2 | 3/2016 | Wilson et al. |
| 9,295,547 B2 | 3/2016 | Costello et al. |
| 9,301,836 B2 | 4/2016 | Buchbinder et al. |
| 9,308,087 B2 | 4/2016 | Lane et al. |
| 9,326,850 B2 | 5/2016 | Venkatasubramanian |
| 9,339,378 B2 | 5/2016 | Quadri et al. |
| 9,339,379 B2 | 5/2016 | Quadri et al. |
| 9,339,380 B2 | 5/2016 | Quadri et al. |
| 9,339,382 B2 | 5/2016 | Tabor et al. |
| 9,358,108 B2 | 6/2016 | Bortlein et al. |
| 9,387,075 B2 | 7/2016 | Bortlein et al. |

(56) References Cited

U.S. PATENT DOCUMENTS

| | | | |
|---|---|---|---|
| 9,387,078 B2 | 7/2016 | Gross et al. |
| 9,393,111 B2 | 7/2016 | Ma et al. |
| 9,554,906 B2 | 1/2017 | Aklog et al. |
| 9,610,159 B2 | 4/2017 | Christianson et al. |
| 9,629,719 B2 | 4/2017 | Rothstein et al. |
| 9,675,454 B2 | 6/2017 | Vidlund et al. |
| 9,681,951 B2 | 6/2017 | Ratz et al. |
| 9,687,342 B2 | 6/2017 | Figulla et al. |
| 9,687,343 B2 | 6/2017 | Bortlein et al. |
| 9,693,859 B2 | 7/2017 | Braido et al. |
| 9,693,862 B2 | 7/2017 | Campbell et al. |
| 9,694,121 B2 | 7/2017 | Alexander et al. |
| 9,700,409 B2 | 7/2017 | Braido et al. |
| 9,700,411 B2 | 7/2017 | Klima et al. |
| 9,730,791 B2 | 8/2017 | Ratz et al. |
| 9,730,792 B2 | 8/2017 | Lutter et al. |
| 9,730,794 B2 | 8/2017 | Carpentier et al. |
| 9,744,036 B2 | 8/2017 | Duffy et al. |
| 9,750,605 B2 | 9/2017 | Ganesan et al. |
| 9,750,606 B2 | 9/2017 | Ganesan et al. |
| 9,750,607 B2 | 9/2017 | Ganesan et al. |
| 9,763,657 B2 | 9/2017 | Hacohen et al. |
| 9,763,658 B2 | 9/2017 | Eigler et al. |
| 9,763,782 B2 | 9/2017 | Solem et al. |
| 9,770,328 B2 | 9/2017 | Macoviak et al. |
| 9,827,092 B2 | 11/2017 | Vidlund et al. |
| 9,827,101 B2 | 11/2017 | Solem et al. |
| 9,833,313 B2 | 12/2017 | Board et al. |
| 9,833,315 B2* | 12/2017 | Vidlund ............ A61F 2/2427 |
| 9,839,511 B2 | 12/2017 | Ma et al. |
| 9,844,435 B2 | 12/2017 | Eidenschink |
| 9,848,880 B2 | 12/2017 | Coleman et al. |
| 9,848,983 B2 | 12/2017 | Lashinski et al. |
| 9,861,477 B2 | 1/2018 | Backus et al. |
| 9,861,480 B2 | 1/2018 | Zakai et al. |
| 9,895,221 B2 | 2/2018 | Vidlund et al. |
| 9,986,993 B2* | 6/2018 | Vidlund ............ A61F 2/2457 |
| 10,080,659 B1 | 9/2018 | Zentgraf et al. |
| 10,085,835 B2 | 10/2018 | Thambar et al. |
| 10,123,874 B2 | 11/2018 | Khairkhahan et al. |
| 10,265,172 B2* | 4/2019 | Krivoruchko ......... A61F 2/2418 |
| 10,610,356 B2* | 4/2020 | Vidlund ............ A61F 2/2418 |
| 10,813,747 B2* | 10/2020 | Wilson ............ A61F 2/0077 |
| 11,033,390 B2* | 6/2021 | Krivoruchko ...... A61B 17/0401 |
| 11,464,628 B2* | 10/2022 | Vidlund ............ A61F 2/2439 |
| 11,759,318 B2* | 9/2023 | Vidlund ............ A61F 2/2418 623/1.14 |
| 2001/0021872 A1 | 9/2001 | Bailey et al. |
| 2001/0049492 A1 | 12/2001 | Frazier et al. |
| 2002/0007219 A1 | 1/2002 | Merrill et al. |
| 2002/0013571 A1 | 1/2002 | Goldfarb et al. |
| 2002/0072792 A1 | 6/2002 | Burgermeister et al. |
| 2002/0082637 A1 | 6/2002 | Lumauig |
| 2002/0099439 A1 | 7/2002 | Schwartz et al. |
| 2002/0138138 A1 | 9/2002 | Yang |
| 2002/0151970 A1 | 10/2002 | Garrison et al. |
| 2002/0173841 A1 | 11/2002 | Ortiz et al. |
| 2003/0078653 A1 | 4/2003 | Vesely |
| 2003/0120340 A1 | 6/2003 | Liska et al. |
| 2003/0139689 A1 | 7/2003 | Shturman et al. |
| 2004/0006358 A1 | 1/2004 | Wulfman et al. |
| 2004/0039412 A1 | 2/2004 | Isshiki et al. |
| 2004/0044350 A1 | 3/2004 | Martin et al. |
| 2004/0057955 A1 | 3/2004 | O'Brien et al. |
| 2004/0082910 A1 | 4/2004 | Constantz et al. |
| 2004/0092858 A1 | 5/2004 | Wilson et al. |
| 2004/0092962 A1 | 5/2004 | Thornton et al. |
| 2004/0092989 A1 | 5/2004 | Wilson et al. |
| 2004/0106989 A1 | 6/2004 | Wilson et al. |
| 2004/0117009 A1 | 6/2004 | Cali et al. |
| 2004/0122510 A1 | 6/2004 | Sarac |
| 2004/0127979 A1 | 7/2004 | Wilson et al. |
| 2004/0127982 A1 | 7/2004 | Machold et al. |
| 2004/0186558 A1 | 9/2004 | Pavcnik et al. |
| 2004/0199191 A1 | 10/2004 | Schwartz |
| 2004/0230117 A1 | 11/2004 | Tosaya et al. |
| 2004/0230212 A1 | 11/2004 | Wulfman |
| 2004/0230213 A1 | 11/2004 | Wulfman et al. |
| 2004/0243162 A1 | 12/2004 | Wulfman et al. |
| 2005/0007219 A1 | 1/2005 | Ma et al. |
| 2005/0075662 A1 | 4/2005 | Pedersen et al. |
| 2005/0075720 A1 | 4/2005 | Nguyen et al. |
| 2005/0075727 A1* | 4/2005 | Wheatley ............ A61F 2/2457 623/902 |
| 2005/0107661 A1 | 5/2005 | Lau et al. |
| 2005/0137682 A1 | 6/2005 | Justino |
| 2005/0137690 A1 | 6/2005 | Salahieh et al. |
| 2005/0137691 A1 | 6/2005 | Salahieh et al. |
| 2005/0137695 A1 | 6/2005 | Salahieh et al. |
| 2005/0137697 A1 | 6/2005 | Salahieh et al. |
| 2005/0137698 A1 | 6/2005 | Salahieh et al. |
| 2005/0137700 A1 | 6/2005 | Spence et al. |
| 2005/0137701 A1 | 6/2005 | Salahieh et al. |
| 2005/0137702 A1 | 6/2005 | Haug et al. |
| 2005/0228477 A1 | 10/2005 | Grainer et al. |
| 2005/0267523 A1 | 12/2005 | Devellian et al. |
| 2005/0273135 A1 | 12/2005 | Chanduszko |
| 2006/0058872 A1 | 3/2006 | Salahieh et al. |
| 2006/0106456 A9 | 5/2006 | Machold et al. |
| 2006/0149360 A1 | 7/2006 | Schwammenthal et al. |
| 2006/0167543 A1 | 7/2006 | Bailey et al. |
| 2006/0195183 A1 | 8/2006 | Navia et al. |
| 2006/0253191 A1 | 11/2006 | Salahieh et al. |
| 2006/0287719 A1 | 12/2006 | Rowe et al. |
| 2007/0056346 A1 | 3/2007 | Spencer et al. |
| 2007/0061010 A1 | 3/2007 | Hauser et al. |
| 2007/0073391 A1 | 3/2007 | Bourang et al. |
| 2007/0078302 A1 | 4/2007 | Ortiz et al. |
| 2007/0088431 A1 | 4/2007 | Bourang et al. |
| 2007/0142906 A1 | 6/2007 | Figulla et al. |
| 2007/0161846 A1 | 7/2007 | Nikolic |
| 2007/0173932 A1 | 7/2007 | Cali et al. |
| 2007/0208217 A1* | 9/2007 | Walsh ............ A61F 2/2481 600/37 |
| 2008/0071369 A1 | 3/2008 | Tuval et al. |
| 2008/0081944 A1* | 4/2008 | Lau ............ A61F 2/2481 600/37 |
| 2008/0082166 A1 | 4/2008 | Styrc et al. |
| 2008/0097595 A1* | 4/2008 | Gabbay ............ A61B 17/3417 604/532 |
| 2008/0103586 A1 | 5/2008 | Styrc et al. |
| 2008/0140189 A1 | 6/2008 | Nguyen et al. |
| 2008/0208217 A1 | 8/2008 | Adams |
| 2008/0208332 A1 | 8/2008 | Lamphere et al. |
| 2008/0221672 A1 | 9/2008 | Lamphere et al. |
| 2008/0234728 A1 | 9/2008 | Starksen et al. |
| 2008/0243245 A1 | 10/2008 | Thambar et al. |
| 2008/0243246 A1 | 10/2008 | Ryan et al. |
| 2009/0048480 A1 | 2/2009 | Klenk |
| 2009/0054969 A1 | 2/2009 | Salahieh et al. |
| 2009/0076586 A1 | 3/2009 | Hauser et al. |
| 2009/0076598 A1 | 3/2009 | Salahieh et al. |
| 2009/0093670 A1 | 4/2009 | Annest et al. |
| 2009/0157174 A1 | 6/2009 | Yoganathan et al. |
| 2009/0164006 A1 | 6/2009 | Seguin et al. |
| 2009/0198315 A1 | 8/2009 | Boudjemline |
| 2009/0216312 A1 | 8/2009 | Straubinger et al. |
| 2009/0240320 A1 | 9/2009 | Tuval et al. |
| 2009/0259292 A1 | 10/2009 | Bonhoeffer |
| 2009/0259306 A1 | 10/2009 | Rowe |
| 2009/0264997 A1 | 10/2009 | Salahieh et al. |
| 2009/0276040 A1 | 11/2009 | Rowe et al. |
| 2009/0281609 A1 | 11/2009 | Benichou et al. |
| 2009/0281618 A1 | 11/2009 | Hill et al. |
| 2009/0292350 A1 | 11/2009 | Eberhardt et al. |
| 2009/0306768 A1 | 12/2009 | Quadri |
| 2009/0319037 A1 | 12/2009 | Rowe et al. |
| 2009/0319038 A1 | 12/2009 | Gurskis et al. |
| 2010/0016958 A1 | 1/2010 | St. Goar et al. |
| 2010/0023115 A1 | 1/2010 | Robaina et al. |
| 2010/0023117 A1* | 1/2010 | Yoganathan ......... A61F 2/2457 623/2.37 |
| 2010/0030330 A1 | 2/2010 | Bobo et al. |
| 2010/0049313 A1 | 2/2010 | Alon et al. |

(56) References Cited

U.S. PATENT DOCUMENTS

| | | |
|---|---|---|
| 2010/0063586 A1 | 3/2010 | Hasenkam et al. |
| 2010/0076548 A1 | 3/2010 | Konno |
| 2010/0082094 A1 | 4/2010 | Quadri et al. |
| 2010/0094411 A1 | 4/2010 | Tuval et al. |
| 2010/0121436 A1 | 5/2010 | Tuval et al. |
| 2010/0185275 A1 | 7/2010 | Richter et al. |
| 2010/0217382 A1 | 8/2010 | Chau et al. |
| 2010/0249915 A1 | 9/2010 | Zhang |
| 2010/0249923 A1 | 9/2010 | Alkhatib et al. |
| 2010/0298929 A1 | 11/2010 | Thornton et al. |
| 2010/0298931 A1 | 11/2010 | Quadri et al. |
| 2010/0312333 A1 | 12/2010 | Navia et al. |
| 2010/0324554 A1 | 12/2010 | Gifford et al. |
| 2011/0004296 A1* | 1/2011 | Lutter .................. A61F 2/2418 623/1.26 |
| 2011/0015722 A1 | 1/2011 | Hauser et al. |
| 2011/0022166 A1 | 1/2011 | Dahlgren et al. |
| 2011/0029071 A1* | 2/2011 | Zlotnick .......... A61B 17/00234 623/2.11 |
| 2011/0029072 A1 | 2/2011 | Gabbay |
| 2011/0040374 A1 | 2/2011 | Goetz et al. |
| 2011/0040375 A1 | 2/2011 | Letac et al. |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137409 A1 | 6/2011 | Yang et al. |
| 2011/0137410 A1 | 6/2011 | Hacohen |
| 2011/0153008 A1 | 6/2011 | Marchand et al. |
| 2011/0172784 A1 | 7/2011 | Richter et al. |
| 2011/0184512 A1 | 7/2011 | Webler et al. |
| 2011/0208293 A1 | 8/2011 | Tabor |
| 2011/0208298 A1 | 8/2011 | Tuval et al. |
| 2011/0224785 A1 | 9/2011 | Hacohen |
| 2011/0319988 A1 | 12/2011 | Schankereli et al. |
| 2012/0022639 A1 | 1/2012 | Hacohen et al. |
| 2012/0035703 A1 | 2/2012 | Lutter et al. |
| 2012/0035713 A1 | 2/2012 | Lutter et al. |
| 2012/0053680 A1 | 3/2012 | Bolling et al. |
| 2012/0053682 A1 | 3/2012 | Kovalsky et al. |
| 2012/0078347 A1 | 3/2012 | Braido et al. |
| 2012/0078360 A1 | 3/2012 | Rafiee |
| 2012/0101571 A1 | 4/2012 | Thambar et al. |
| 2012/0165930 A1 | 6/2012 | Gifford, III et al. |
| 2012/0179239 A1 | 7/2012 | Quadri |
| 2012/0179244 A1 | 7/2012 | Schankereli et al. |
| 2012/0203336 A1 | 8/2012 | Annest |
| 2012/0283824 A1 | 11/2012 | Lutter et al. |
| 2013/0079873 A1 | 3/2013 | Migliazza et al. |
| 2013/0172978 A1* | 7/2013 | Vidlund ............. A61B 17/0401 623/1.12 |
| 2013/0190860 A1* | 7/2013 | Sundt, III ............. A61F 2/2412 623/2.18 |
| 2013/0190861 A1 | 7/2013 | Chau et al. |
| 2013/0197354 A1 | 8/2013 | Maschke et al. |
| 2013/0197630 A1 | 8/2013 | Azarnoush |
| 2013/0204356 A1 | 8/2013 | Dwork et al. |
| 2013/0204358 A1 | 8/2013 | Matheny |
| 2013/0226289 A1 | 8/2013 | Shaolian et al. |
| 2013/0226290 A1 | 8/2013 | Yellin et al. |
| 2013/0231735 A1 | 9/2013 | Deem et al. |
| 2013/0238089 A1 | 9/2013 | Lichtenstein et al. |
| 2013/0244927 A1 | 9/2013 | Lal et al. |
| 2013/0253641 A1 | 9/2013 | Lattouf |
| 2013/0253642 A1 | 9/2013 | Brecker |
| 2013/0253643 A1 | 9/2013 | Rolando et al. |
| 2013/0259337 A1 | 10/2013 | Guhring et al. |
| 2013/0261737 A1 | 10/2013 | Costello |
| 2013/0261738 A1 | 10/2013 | Clague et al. |
| 2013/0261739 A1 | 10/2013 | Kuehn |
| 2013/0261741 A1 | 10/2013 | Accola |
| 2013/0268066 A1 | 10/2013 | Rowe |
| 2013/0274870 A1 | 10/2013 | Lombardi et al. |
| 2013/0282059 A1 | 10/2013 | Ketai et al. |
| 2013/0282060 A1 | 10/2013 | Tuval |
| 2013/0282110 A1 | 10/2013 | Schweich, Jr. et al. |
| 2013/0289642 A1 | 10/2013 | Hedberg et al. |
| 2013/0289717 A1* | 10/2013 | Solem ................. A61M 60/187 623/2.11 |
| 2013/0289718 A1 | 10/2013 | Tsukashima et al. |
| 2013/0296851 A1 | 11/2013 | Boronyak et al. |
| 2013/0296999 A1 | 11/2013 | Burriesci et al. |
| 2013/0304180 A1 | 11/2013 | Green et al. |
| 2013/0304181 A1 | 11/2013 | Green et al. |
| 2013/0304197 A1 | 11/2013 | Buchbinder et al. |
| 2013/0304198 A1 | 11/2013 | Solem |
| 2013/0304200 A1 | 11/2013 | Mclean et al. |
| 2013/0309292 A1 | 11/2013 | Andersen |
| 2013/0310436 A1 | 11/2013 | Lowes et al. |
| 2013/0310925 A1 | 11/2013 | Eliasen et al. |
| 2013/0310928 A1 | 11/2013 | Morriss et al. |
| 2013/0317603 A1 | 11/2013 | Mclean et al. |
| 2013/0325110 A1 | 12/2013 | Khalil et al. |
| 2013/0325114 A1 | 12/2013 | Mclean et al. |
| 2013/0331864 A1 | 12/2013 | Jelich et al. |
| 2013/0338684 A1 | 12/2013 | Hausen |
| 2013/0338763 A1* | 12/2013 | Rowe ..................... A61F 2/246 623/2.11 |
| 2013/0345797 A1 | 12/2013 | Dahlgren et al. |
| 2013/0345803 A1 | 12/2013 | Bergheim, III |
| 2014/0005778 A1 | 1/2014 | Buchbinder et al. |
| 2014/0018906 A1 | 1/2014 | Rafiee |
| 2014/0018913 A1 | 1/2014 | Cartledge et al. |
| 2014/0023261 A1 | 1/2014 | Watanabe et al. |
| 2014/0025164 A1 | 1/2014 | Montorfano et al. |
| 2014/0031928 A1* | 1/2014 | Murphy ................ A61F 2/246 623/2.37 |
| 2014/0046219 A1 | 2/2014 | Sauter et al. |
| 2014/0046436 A1 | 2/2014 | Kheradvar |
| 2014/0052237 A1 | 2/2014 | Lane et al. |
| 2014/0052240 A1 | 2/2014 | Zhang |
| 2014/0056906 A1 | 2/2014 | Yue et al. |
| 2014/0066895 A1 | 3/2014 | Kipperman |
| 2014/0067048 A1 | 3/2014 | Chau et al. |
| 2014/0067052 A1 | 3/2014 | Chau et al. |
| 2014/0067054 A1 | 3/2014 | Chau et al. |
| 2014/0088071 A1 | 3/2014 | Nakai et al. |
| 2014/0088680 A1 | 3/2014 | Costello et al. |
| 2014/0088693 A1 | 3/2014 | Seguin et al. |
| 2014/0088695 A1 | 3/2014 | Figulla et al. |
| 2014/0094906 A1 | 4/2014 | Spence et al. |
| 2014/0107775 A1 | 4/2014 | Hjelle et al. |
| 2014/0114404 A1 | 4/2014 | Gammie et al. |
| 2014/0114407 A1 | 4/2014 | Rajamannan |
| 2014/0121763 A1 | 5/2014 | Duffy et al. |
| 2014/0128965 A1 | 5/2014 | Rafiee |
| 2014/0135913 A1 | 5/2014 | Lichtenstein et al. |
| 2014/0163652 A1 | 6/2014 | Witzel et al. |
| 2014/0163668 A1 | 6/2014 | Rafiee |
| 2014/0172076 A1 | 6/2014 | Jonsson et al. |
| 2014/0172084 A1 | 6/2014 | Callas et al. |
| 2014/0172085 A1 | 6/2014 | Quadri et al. |
| 2014/0172086 A1 | 6/2014 | Quadri et al. |
| 2014/0179993 A1 | 6/2014 | Alexander et al. |
| 2014/0180401 A1 | 6/2014 | Quill et al. |
| 2014/0188108 A1 | 7/2014 | Goodine et al. |
| 2014/0188215 A1 | 7/2014 | Hlavka et al. |
| 2014/0194920 A1 | 7/2014 | Krahbichler |
| 2014/0194976 A1 | 7/2014 | Starksen et al. |
| 2014/0200397 A1 | 7/2014 | Raman et al. |
| 2014/0200649 A1 | 7/2014 | Essinger et al. |
| 2014/0200657 A1 | 7/2014 | Maurer et al. |
| 2014/0200662 A1 | 7/2014 | Eftel et al. |
| 2014/0214159 A1* | 7/2014 | Vidlund ................ A61F 2/2418 623/2.14 |
| 2014/0219524 A1 | 8/2014 | Takeguchi et al. |
| 2014/0222040 A1 | 8/2014 | Park et al. |
| 2014/0222138 A1 | 8/2014 | Machold et al. |
| 2014/0228942 A1 | 8/2014 | Krahbichler |
| 2014/0228946 A1 | 8/2014 | Chau et al. |
| 2014/0242086 A1 | 8/2014 | Lal et al. |
| 2014/0243860 A1 | 8/2014 | Morris et al. |
| 2014/0243954 A1 | 8/2014 | Shannon |
| 2014/0243964 A1 | 8/2014 | Venkatasubramanian |

(56) References Cited

U.S. PATENT DOCUMENTS

| | | | |
|---|---|---|---|
| 2014/0249621 A1* | 9/2014 | Eidenschink | A61F 2/2439 623/2.11 |
| 2014/0257101 A1 | 9/2014 | Gaudiani | |
| 2014/0257466 A1 | 9/2014 | Board et al. | |
| 2014/0257467 A1 | 9/2014 | Lane et al. | |
| 2014/0257473 A1 | 9/2014 | Rajamannan | |
| 2014/0257475 A1 | 9/2014 | Gross et al. | |
| 2014/0275757 A1 | 9/2014 | Goodwin et al. | |
| 2014/0276395 A1 | 9/2014 | Wilson et al. | |
| 2014/0276609 A1 | 9/2014 | Magee et al. | |
| 2014/0276782 A1 | 9/2014 | Paskar | |
| 2014/0276971 A1 | 9/2014 | Kovach | |
| 2014/0277119 A1 | 9/2014 | Akpinar | |
| 2014/0277390 A1 | 9/2014 | Ratz et al. | |
| 2014/0277404 A1* | 9/2014 | Wilson | A61F 2/2427 623/2.11 |
| 2014/0277405 A1 | 9/2014 | Wilson et al. | |
| 2014/0277406 A1 | 9/2014 | Arcidi | |
| 2014/0277407 A1 | 9/2014 | Dale et al. | |
| 2014/0277408 A1 | 9/2014 | Folan | |
| 2014/0277409 A1 | 9/2014 | Bortlein et al. | |
| 2014/0277410 A1 | 9/2014 | Bortlein et al. | |
| 2014/0277411 A1 | 9/2014 | Bortlein et al. | |
| 2014/0277412 A1 | 9/2014 | Bortlein et al. | |
| 2014/0277420 A1 | 9/2014 | Migliazza et al. | |
| 2014/0277422 A1 | 9/2014 | Ratz et al. | |
| 2014/0288480 A1 | 9/2014 | Zimmerman et al. | |
| 2014/0296878 A1 | 10/2014 | Oz et al. | |
| 2014/0296969 A1* | 10/2014 | Tegels | A61F 2/2412 623/2.11 |
| 2014/0296970 A1* | 10/2014 | Ekvall | A61F 2/2436 623/2.11 |
| 2014/0296971 A1 | 10/2014 | Tegels et al. | |
| 2014/0296975 A1* | 10/2014 | Tegels | A61F 2/07 623/2.18 |
| 2014/0303719 A1 | 10/2014 | Cox et al. | |
| 2014/0303721 A1 | 10/2014 | Fung et al. | |
| 2014/0309727 A1 | 10/2014 | Lamelas et al. | |
| 2014/0309730 A1 | 10/2014 | Alon et al. | |
| 2014/0309731 A1 | 10/2014 | Quadri et al. | |
| 2014/0309732 A1 | 10/2014 | Solem | |
| 2014/0316516 A1 | 10/2014 | Vidlund et al. | |
| 2014/0324164 A1 | 10/2014 | Gross et al. | |
| 2014/0358222 A1 | 12/2014 | Gorman, III et al. | |
| 2014/0358224 A1* | 12/2014 | Tegels | A61L 27/54 623/2.14 |
| 2014/0364944 A1 | 12/2014 | Lutter et al. | |
| 2014/0371843 A1 | 12/2014 | Wilson et al. | |
| 2014/0371844 A1 | 12/2014 | Dale et al. | |
| 2014/0371846 A1 | 12/2014 | Wilson et al. | |
| 2014/0379074 A1 | 12/2014 | Spence et al. | |
| 2014/0379076 A1* | 12/2014 | Vidlund | A61F 2/2412 623/2.18 |
| 2015/0005874 A1* | 1/2015 | Vidlund | A61F 2/2412 623/2.14 |
| 2015/0005875 A1 | 1/2015 | Tuval et al. | |
| 2015/0018607 A1* | 1/2015 | Akita | D04B 1/18 600/37 |
| 2015/0025623 A1 | 1/2015 | Granada et al. | |
| 2015/0032127 A1 | 1/2015 | Gammie et al. | |
| 2015/0045878 A1 | 2/2015 | Rowe | |
| 2015/0057705 A1 | 2/2015 | Vidlund | |
| 2015/0066140 A1 | 3/2015 | Quadri et al. | |
| 2015/0094802 A1 | 4/2015 | Buchbinder et al. | |
| 2015/0094803 A1 | 4/2015 | Navia | |
| 2015/0100116 A1 | 4/2015 | Mohl et al. | |
| 2015/0112427 A1 | 4/2015 | Schweich, Jr. et al. | |
| 2015/0112429 A1 | 4/2015 | Khairkhahan et al. | |
| 2015/0112433 A1 | 4/2015 | Schweich, Jr. et al. | |
| 2015/0119978 A1 | 4/2015 | Tegels et al. | |
| 2015/0119981 A1 | 4/2015 | Khairkhahan et al. | |
| 2015/0119982 A1 | 4/2015 | Quill et al. | |
| 2015/0127091 A1 | 5/2015 | Cecere et al. | |
| 2015/0127096 A1 | 5/2015 | Rowe et al. | |
| 2015/0142101 A1* | 5/2015 | Coleman | A61B 17/12109 623/2.11 |
| 2015/0142103 A1* | 5/2015 | Vidlund | A61F 2/2418 623/2.17 |
| 2015/0142105 A1 | 5/2015 | Bolling et al. | |
| 2015/0150678 A1 | 6/2015 | Brecker | |
| 2015/0157458 A1 | 6/2015 | Thambar et al. | |
| 2015/0157459 A1 | 6/2015 | Macoviak et al. | |
| 2015/0164637 A1 | 6/2015 | Khairkhahan et al. | |
| 2015/0164641 A1 | 6/2015 | Annest | |
| 2015/0173897 A1 | 6/2015 | Raanani et al. | |
| 2015/0173898 A1 | 6/2015 | Drasler et al. | |
| 2015/0173900 A1 | 6/2015 | Hauser et al. | |
| 2015/0190229 A1 | 7/2015 | Seguin | |
| 2015/0196390 A1 | 7/2015 | Ma et al. | |
| 2015/0196393 A1 | 7/2015 | Vidlund et al. | |
| 2015/0202043 A1 | 7/2015 | Zakai et al. | |
| 2015/0209137 A1 | 7/2015 | Quadri et al. | |
| 2015/0209139 A1 | 7/2015 | Granada et al. | |
| 2015/0216655 A1 | 8/2015 | Lane et al. | |
| 2015/0216661 A1 | 8/2015 | Hacohen et al. | |
| 2015/0223802 A1 | 8/2015 | Tegzes | |
| 2015/0223934 A1* | 8/2015 | Vidlund | A61B 17/0401 623/2.11 |
| 2015/0223935 A1 | 8/2015 | Subramanian et al. | |
| 2015/0230920 A1 | 8/2015 | Alfieri et al. | |
| 2015/0230921 A1 | 8/2015 | Chau et al. | |
| 2015/0238312 A1 | 8/2015 | Lashinski | |
| 2015/0238313 A1 | 8/2015 | Spence et al. | |
| 2015/0250461 A1 | 9/2015 | Berreklouw | |
| 2015/0250590 A1 | 9/2015 | Gries et al. | |
| 2015/0257877 A1 | 9/2015 | Hernandez | |
| 2015/0257878 A1 | 9/2015 | Lane et al. | |
| 2015/0257879 A1 | 9/2015 | Bortlein et al. | |
| 2015/0257881 A1 | 9/2015 | Bortlein et al. | |
| 2015/0257882 A1 | 9/2015 | Bortlein et al. | |
| 2015/0272737 A1 | 10/2015 | Dale et al. | |
| 2015/0305861 A1 | 10/2015 | Annest | |
| 2015/0305864 A1 | 10/2015 | Quadri et al. | |
| 2015/0313739 A1 | 11/2015 | Hummen et al. | |
| 2015/0320553 A1 | 11/2015 | Chau et al. | |
| 2015/0327999 A1 | 11/2015 | Board et al. | |
| 2015/0328000 A1 | 11/2015 | Ratz et al. | |
| 2015/0342733 A1 | 12/2015 | Alkhatib et al. | |
| 2015/0342737 A1* | 12/2015 | Biancucci | A61F 2/2481 600/37 |
| 2015/0351906 A1 | 12/2015 | Hammer et al. | |
| 2015/0351908 A1 | 12/2015 | Keranen et al. | |
| 2015/0359628 A1 | 12/2015 | Keranen | |
| 2015/0359629 A1 | 12/2015 | Ganesan et al. | |
| 2015/0359631 A1 | 12/2015 | Sheahan et al. | |
| 2015/0366666 A1 | 12/2015 | Khairkhahan et al. | |
| 2015/0374495 A1 | 12/2015 | Ruyra Baliarda et al. | |
| 2016/0000983 A1 | 1/2016 | Mohl et al. | |
| 2016/0015513 A1 | 1/2016 | Lashinski et al. | |
| 2016/0015514 A1 | 1/2016 | Lashinski et al. | |
| 2016/0015515 A1 | 1/2016 | Lashinski et al. | |
| 2016/0015543 A1 | 1/2016 | Perouse et al. | |
| 2016/0030171 A1 | 2/2016 | Quijano et al. | |
| 2016/0038246 A1 | 2/2016 | Wang et al. | |
| 2016/0038280 A1 | 2/2016 | Morriss et al. | |
| 2016/0038283 A1 | 2/2016 | Divekar et al. | |
| 2016/0038286 A1 | 2/2016 | Yellin et al. | |
| 2016/0074160 A1* | 3/2016 | Christianson | A61F 2/2409 623/2.18 |
| 2016/0106539 A1 | 4/2016 | Buchbinder et al. | |
| 2016/0113764 A1 | 4/2016 | Sheahan et al. | |
| 2016/0113765 A1 | 4/2016 | Ganesan et al. | |
| 2016/0113766 A1 | 4/2016 | Ganesan et al. | |
| 2016/0113768 A1 | 4/2016 | Ganesan et al. | |
| 2016/0120643 A1 | 5/2016 | Kupumbati | |
| 2016/0143730 A1 | 5/2016 | Kheradvar | |
| 2016/0143736 A1* | 5/2016 | Vidlund | A61B 17/0057 623/2.4 |
| 2016/0151154 A1 | 6/2016 | Gorman, III et al. | |
| 2016/0151156 A1 | 6/2016 | Seguin et al. | |
| 2016/0151552 A1 | 6/2016 | Solem | |
| 2016/0157999 A1 | 6/2016 | Lane et al. | |
| 2016/0158000 A1 | 6/2016 | Granada et al. | |

(56) References Cited

U.S. PATENT DOCUMENTS

| | | |
|---|---|---|
| 2016/0158001 A1 | 6/2016 | Wallace et al. |
| 2016/0158002 A1 | 6/2016 | Wallace et al. |
| 2016/0158003 A1 | 6/2016 | Wallace et al. |
| 2016/0184095 A1 | 6/2016 | Spence et al. |
| 2016/0206280 A1 | 7/2016 | Vidlund et al. |
| 2016/0206424 A1* | 7/2016 | Al-Jilaihawi ......... A61F 2/2418 |
| 2016/0213828 A1 | 7/2016 | Sievers |
| 2016/0262881 A1 | 9/2016 | Schankereli et al. |
| 2016/0317290 A1 | 11/2016 | Chau et al. |
| 2016/0324635 A1* | 11/2016 | Vidlund ................ A61F 2/2433 |
| 2017/0079790 A1* | 3/2017 | Vidlund ............ A61B 17/0401 |
| 2017/0100248 A1 | 4/2017 | Tegels et al. |
| 2017/0100250 A1 | 4/2017 | Marsot et al. |
| 2017/0119526 A1 | 5/2017 | Luong et al. |
| 2017/0128198 A1 | 5/2017 | Cartledge et al. |
| 2017/0128205 A1 | 5/2017 | Tamir et al. |
| 2017/0128206 A1 | 5/2017 | Rafiee et al. |
| 2017/0128208 A1* | 5/2017 | Christianson ......... A61F 2/2457 |
| 2017/0156860 A1 | 6/2017 | Lashinski |
| 2017/0165054 A1 | 6/2017 | Benson et al. |
| 2017/0165055 A1 | 6/2017 | Hauser et al. |
| 2017/0165064 A1 | 6/2017 | Nyuli et al. |
| 2017/0172737 A1* | 6/2017 | Kuetting ............... A61F 2/2418 |
| 2017/0181851 A1 | 6/2017 | Annest |
| 2017/0189177 A1 | 7/2017 | Schweich, Jr. et al. |
| 2017/0189179 A1 | 7/2017 | Ratz et al. |
| 2017/0189180 A1 | 7/2017 | Alkhatib |
| 2017/0189181 A1 | 7/2017 | Alkhatib et al. |
| 2017/0196688 A1 | 7/2017 | Christianson et al. |
| 2017/0231762 A1 | 8/2017 | Quadri et al. |
| 2017/0231763 A1 | 8/2017 | Yellin et al. |
| 2017/0258585 A1 | 9/2017 | Marquez et al. |
| 2017/0266001 A1 | 9/2017 | Vidlund et al. |
| 2017/0281343 A1* | 10/2017 | Christianson ......... A61F 2/2439 |
| 2017/0281345 A1 | 10/2017 | Yang et al. |
| 2017/0290659 A1 | 10/2017 | Ulmer et al. |
| 2017/0296339 A1 | 10/2017 | Thambar et al. |
| 2017/0312077 A1* | 11/2017 | Vidlund ................ A61F 2/2439 |
| 2017/0312078 A1* | 11/2017 | Krivoruchko ......... A61F 2/2418 |
| 2017/0319333 A1* | 11/2017 | Tegels ................ A61B 17/0401 |
| 2017/0325941 A1 | 11/2017 | Wallace et al. |
| 2017/0325945 A1 | 11/2017 | Dale et al. |
| 2017/0325948 A1 | 11/2017 | Wallace et al. |
| 2017/0333186 A1 | 11/2017 | Spargias |
| 2017/0333188 A1 | 11/2017 | Carpentier et al. |
| 2017/0340440 A1 | 11/2017 | Ratz et al. |
| 2017/0348098 A1 | 12/2017 | Rowe et al. |
| 2017/0348100 A1 | 12/2017 | Lane et al. |
| 2017/0354496 A1 | 12/2017 | Quadri et al. |
| 2017/0354497 A1 | 12/2017 | Quadri et al. |
| 2017/0354499 A1 | 12/2017 | Granada et al. |
| 2017/0360426 A1 | 12/2017 | Hacohen et al. |
| 2017/0360549 A1 | 12/2017 | Lashinski et al. |
| 2017/0360558 A1 | 12/2017 | Ma |
| 2017/0360585 A1 | 12/2017 | White |
| 2018/0078370 A1* | 3/2018 | Kovalsky .............. A61F 2/2433 |
| 2018/0185141 A1* | 7/2018 | Wilson .................. A61F 2/0077 |
| 2018/0289478 A1* | 10/2018 | Quill .................... A61F 2/2436 |
| 2018/0360439 A1* | 12/2018 | Niland ............... A61B 17/0483 |
| 2020/0022810 A1* | 1/2020 | Christianson .... A61B 17/00234 |
| 2020/0085574 A1* | 3/2020 | Reimer ................ A61F 2/2454 |
| 2020/0179112 A1* | 6/2020 | Vidlund ............. A61B 17/0487 |
| 2020/0188093 A1* | 6/2020 | Wang .................... A61F 2/2412 |
| 2020/0237514 A1* | 7/2020 | Kofidis ................ A61F 2/2415 |
| 2020/0282204 A1* | 9/2020 | Capek .................. A61N 1/3629 |
| 2021/0022855 A1* | 1/2021 | Tegels ................. A61F 2/2418 |
| 2021/0169645 A1* | 6/2021 | Dale ................. A61B 17/0401 |
| 2021/0220130 A1* | 7/2021 | Rajagopal ............ A61F 2/2466 |
| 2021/0228354 A1* | 7/2021 | Rafiee .................. A61F 2/2454 |
| 2021/0298899 A1* | 9/2021 | Huddleston ........ A61B 17/3468 |
| 2022/0047387 A1* | 2/2022 | Kofidis ................ A61F 2/2412 |
| 2022/0079751 A1* | 3/2022 | Yao ...................... A61F 2/2457 |
| 2022/0079754 A1* | 3/2022 | Mei ...................... A61F 2/2466 |
| 2022/0104941 A1* | 4/2022 | Rajagopal ............ A61F 2/2466 |
| 2022/0313427 A1* | 10/2022 | Vidlund ................ A61F 2/2457 |
| 2022/0331097 A1* | 10/2022 | King .................... A61F 2/2457 |
| 2023/0294301 A1* | 9/2023 | Kim ..................... B25J 19/0075 |
| | | 700/258 |

FOREIGN PATENT DOCUMENTS

| | | |
|---|---|---|
| CN | 101291637 | 10/2008 |
| CN | 103491900 | 1/2014 |
| DE | 19605042 | 1/1998 |
| DE | 102006052564 | 12/2007 |
| EP | 186104 | 7/1986 |
| EP | 1512383 | 3/2005 |
| EP | 1545371 | 6/2005 |
| EP | 1551274 | 7/2005 |
| EP | 1629794 | 3/2006 |
| EP | 1646332 | 4/2006 |
| EP | 1702247 | 9/2006 |
| EP | 1734903 | 12/2006 |
| EP | 1891914 | 2/2008 |
| EP | 2026280 | 2/2009 |
| EP | 2037829 | 3/2009 |
| EP | 2081519 | 7/2009 |
| EP | 2111190 | 10/2009 |
| EP | 2142143 | 1/2010 |
| EP | 2167742 | 3/2010 |
| EP | 2278944 | 2/2011 |
| EP | 2306821 | 4/2011 |
| EP | 2327429 | 6/2011 |
| EP | 2400924 | 1/2012 |
| EP | 2400926 | 1/2012 |
| EP | 2410947 | 2/2012 |
| EP | 2416739 | 2/2012 |
| EP | 2419050 | 2/2012 |
| EP | 2444031 | 4/2012 |
| EP | 2488126 | 8/2012 |
| EP | 2549955 | 1/2013 |
| EP | 2549956 | 1/2013 |
| EP | 2566416 | 3/2013 |
| EP | 2586492 | 5/2013 |
| EP | 2618784 | 7/2013 |
| EP | 2623068 | 8/2013 |
| EP | 2626013 | 8/2013 |
| EP | 2629699 | 8/2013 |
| EP | 2633457 | 9/2013 |
| EP | 2637659 | 9/2013 |
| EP | 2641569 | 9/2013 |
| EP | 2644158 | 10/2013 |
| EP | 2654624 | 10/2013 |
| EP | 2656794 | 10/2013 |
| EP | 2656795 | 10/2013 |
| EP | 2656796 | 10/2013 |
| EP | 2667823 | 12/2013 |
| EP | 2670358 | 12/2013 |
| EP | 2676640 | 12/2013 |
| EP | 2688041 | 1/2014 |
| EP | 2695586 | 2/2014 |
| EP | 2697721 | 2/2014 |
| EP | 2713953 | 4/2014 |
| EP | 2714068 | 4/2014 |
| EP | 2723272 | 4/2014 |
| EP | 2723273 | 4/2014 |
| EP | 2723277 | 4/2014 |
| EP | 2739214 | 6/2014 |
| EP | 2741711 | 6/2014 |
| EP | 2750630 | 7/2014 |
| EP | 2750631 | 7/2014 |
| EP | 2755562 | 7/2014 |
| EP | 2755602 | 7/2014 |
| EP | 2757962 | 7/2014 |
| EP | 2777616 | 9/2014 |
| EP | 2777617 | 9/2014 |
| EP | 2782523 | 10/2014 |
| EP | 2785282 | 10/2014 |
| EP | 2786817 | 10/2014 |
| EP | 2790609 | 10/2014 |
| EP | 2793751 | 10/2014 |
| EP | 2809263 | 12/2014 |
| EP | 2810620 | 12/2014 |

(56) References Cited

FOREIGN PATENT DOCUMENTS

| | | |
|---|---|---|
| EP | 2814428 | 12/2014 |
| EP | 2814429 | 12/2014 |
| EP | 2819617 | 1/2015 |
| EP | 2819618 | 1/2015 |
| EP | 2819619 | 1/2015 |
| EP | 2833836 | 2/2015 |
| EP | 2838475 | 2/2015 |
| EP | 2839815 | 2/2015 |
| EP | 2844190 | 3/2015 |
| EP | 2849680 | 3/2015 |
| EP | 2849681 | 3/2015 |
| EP | 2852354 | 4/2015 |
| EP | 2870933 | 5/2015 |
| EP | 2873011 | 5/2015 |
| EP | 2875797 | 5/2015 |
| EP | 2760375 | 6/2015 |
| EP | 2882374 | 6/2015 |
| EP | 2886082 | 6/2015 |
| EP | 2886083 | 6/2015 |
| EP | 2886084 | 6/2015 |
| EP | 2895111 | 7/2015 |
| EP | 2901966 | 8/2015 |
| EP | 2907479 | 8/2015 |
| EP | 2945572 | 11/2015 |
| EP | 2948094 | 12/2015 |
| EP | 2948102 | 12/2015 |
| EP | 2964152 | 1/2016 |
| EP | 2967859 | 1/2016 |
| EP | 2967860 | 1/2016 |
| EP | 2967866 | 1/2016 |
| EP | 2968847 | 1/2016 |
| EP | 2981208 | 2/2016 |
| EP | 2982336 | 2/2016 |
| EP | 2999433 | 3/2016 |
| EP | 3003187 | 4/2016 |
| EP | 3003219 | 4/2016 |
| EP | 3003220 | 4/2016 |
| EP | 3010447 | 4/2016 |
| EP | 3013281 | 5/2016 |
| EP | 3017792 | 5/2016 |
| EP | 3021792 | 5/2016 |
| EP | 3023117 | 5/2016 |
| EP | 3027143 | 6/2016 |
| EP | 3033048 | 6/2016 |
| EP | 3037064 | 6/2016 |
| EP | 3079633 | 10/2016 |
| EP | 3229736 | 11/2016 |
| EP | 2470119 | 5/2017 |
| EP | 2999436 | 5/2017 |
| EP | 3184081 | 6/2017 |
| EP | 3191027 | 7/2017 |
| EP | 2611389 | 8/2017 |
| EP | 3082656 | 8/2017 |
| EP | 3206628 | 8/2017 |
| EP | 2010103 | 9/2017 |
| EP | 2509538 | 9/2017 |
| EP | 3223751 | 10/2017 |
| EP | 3027144 | 11/2017 |
| EP | 3110368 | 11/2017 |
| EP | 3110369 | 11/2017 |
| EP | 3132773 | 11/2017 |
| EP | 3245980 | 11/2017 |
| EP | 3250154 | 12/2017 |
| EP | 3256077 | 12/2017 |
| EP | 3258883 | 12/2017 |
| EP | 3273910 | 1/2018 |
| JP | 6504516 | 5/1994 |
| JP | H10258124 | 9/1998 |
| JP | 2002509756 | 4/2002 |
| JP | 2005280917 | 10/2005 |
| JP | 2008528117 | 7/2008 |
| JP | 2008541863 | 11/2008 |
| JP | 2009195712 | 9/2009 |
| JP | 2010518947 | 6/2010 |
| JP | 5219518 | 6/2013 |
| WO | WO-1992017118 | 10/1992 |
| WO | WO-1995016407 | 6/1995 |
| WO | WO-1999004730 | 2/1999 |
| WO | WO-1999039648 | 8/1999 |
| WO | WO-1999049799 | 10/1999 |
| WO | WO-2001010343 | 2/2001 |
| WO | WO-2002003892 | 1/2002 |
| WO | WO-2002028421 | 4/2002 |
| WO | WO-2002039908 | 5/2002 |
| WO | WO-2003043685 | 5/2003 |
| WO | WO-2004084746 | 10/2004 |
| WO | WO-2004093728 | 11/2004 |
| WO | WO-2004096097 | 11/2004 |
| WO | WO-2004112657 | 12/2004 |
| WO | WO-2005002466 | 1/2005 |
| WO | WO-2005007219 | 1/2005 |
| WO | WO-2005009285 | 2/2005 |
| WO | WO-2005009506 | 2/2005 |
| WO | WO-2005087140 | 9/2005 |
| WO | WO-2006041877 | 4/2006 |
| WO | WO-2006063199 | 6/2006 |
| WO | WO-2007008371 | 1/2007 |
| WO | WO-2007067820 | 6/2007 |
| WO | 2007098232 | 8/2007 |
| WO | WO-2008022077 | 2/2008 |
| WO | WO-2008028569 | 3/2008 |
| WO | WO-2008035337 | 3/2008 |
| WO | 2008103722 | 8/2008 |
| WO | WO-2008103497 | 8/2008 |
| WO | WO-2008129405 | 10/2008 |
| WO | WO-2009045338 | 4/2009 |
| WO | 2009091509 | 7/2009 |
| WO | WO-2010006627 | 1/2010 |
| WO | WO-2010008549 | 1/2010 |
| WO | WO-2010057262 | 5/2010 |
| WO | WO-2010080594 | 7/2010 |
| WO | WO-2010098857 | 9/2010 |
| WO | WO-2010099032 | 9/2010 |
| WO | 2010121076 | 10/2010 |
| WO | WO-2010117680 | 10/2010 |
| WO | 2011025981 | 3/2011 |
| WO | WO-2011047168 | 4/2011 |
| WO | WO-2011051043 | 5/2011 |
| WO | WO-2011057087 | 5/2011 |
| WO | WO-2011072084 | 6/2011 |
| WO | WO-2011106137 | 9/2011 |
| WO | WO-2011106544 | 9/2011 |
| WO | WO-2011111047 | 9/2011 |
| WO | WO-2011137531 | 11/2011 |
| WO | WO-2011139747 | 11/2011 |
| WO | WO-2012011018 | 1/2012 |
| WO | WO-2012011108 | 1/2012 |
| WO | WO-2012027487 | 3/2012 |
| WO | WO-2012035279 | 3/2012 |
| WO | WO-2012040655 | 3/2012 |
| WO | 2012052718 | 4/2012 |
| WO | WO-2012047644 | 4/2012 |
| WO | WO-2012055498 | 5/2012 |
| WO | WO-2012087842 | 6/2012 |
| WO | WO-2012095455 | 7/2012 |
| WO | WO-2012102928 | 8/2012 |
| WO | WO-2012106602 | 8/2012 |
| WO | WO-2012118508 | 9/2012 |
| WO | WO-2012118816 | 9/2012 |
| WO | WO-2012118894 | 9/2012 |
| WO | WO-2012177942 | 12/2012 |
| WO | WO-2013021374 | 2/2013 |
| WO | WO-2013021375 | 2/2013 |
| WO | WO-2013028387 | 2/2013 |
| WO | WO-2013059743 | 4/2013 |
| WO | WO-2013059747 | 4/2013 |
| WO | WO-2013114214 | 8/2013 |
| WO | WO-2013120181 | 8/2013 |
| WO | WO-2013123059 | 8/2013 |
| WO | WO-2013128432 | 9/2013 |
| WO | WO-2013130641 | 9/2013 |
| WO | WO-2013131925 | 9/2013 |
| WO | WO-2013140318 | 9/2013 |
| WO | WO-2013148017 | 10/2013 |

(56) References Cited

FOREIGN PATENT DOCUMENTS

| | | |
|---|---|---|
| WO | WO-2013148018 | 10/2013 |
| WO | WO-2013148019 | 10/2013 |
| WO | WO-2013150512 | 10/2013 |
| WO | WO-2013152161 | 10/2013 |
| WO | WO-2013158613 | 10/2013 |
| WO | WO-2013169448 | 11/2013 |
| WO | WO-2013175468 | 11/2013 |
| WO | WO-2013176583 | 11/2013 |
| WO | WO-2013188077 | 12/2013 |
| WO | WO-2013192107 | 12/2013 |
| WO | WO-2014036113 | 3/2014 |
| WO | WO-2014043527 | 3/2014 |
| WO | WO-2014047111 | 3/2014 |
| WO | WO-2014047325 | 3/2014 |
| WO | WO-2014055981 | 4/2014 |
| WO | WO-2014059432 | 4/2014 |
| WO | WO-2014064694 | 5/2014 |
| WO | WO-2014066365 | 5/2014 |
| WO | WO-2014089424 | 6/2014 |
| WO | WO-2014093861 | 6/2014 |
| WO | WO-2014111918 | 7/2014 |
| WO | WO-2014114794 | 7/2014 |
| WO | WO-2014114795 | 7/2014 |
| WO | WO-2014114796 | 7/2014 |
| WO | WO-2014114798 | 7/2014 |
| WO | WO-2014116502 | 7/2014 |
| WO | WO-2014121280 | 8/2014 |
| WO | WO-2014128705 | 8/2014 |
| WO | WO-2014134277 | 9/2014 |
| WO | WO-2014138194 | 9/2014 |
| WO | WO-2014138284 | 9/2014 |
| WO | WO-2014138482 | 9/2014 |
| WO | WO-2014138868 | 9/2014 |
| WO | WO-2014144100 | 9/2014 |
| WO | WO-2014144937 | 9/2014 |
| WO | WO-2014145338 | 9/2014 |
| WO | WO-2014147336 | 9/2014 |
| WO | WO-2014152306 | 9/2014 |
| WO | WO-2014152375 | 9/2014 |
| WO | WO-2014152503 | 9/2014 |
| WO | WO-2014153544 | 9/2014 |
| WO | WO-2014158617 | 10/2014 |
| WO | WO-2014162181 | 10/2014 |
| WO | WO-2014162306 | 10/2014 |
| WO | WO-2014163705 | 10/2014 |
| WO | WO-2014168655 | 10/2014 |
| WO | WO-2014179391 | 11/2014 |
| WO | WO-2014181336 | 11/2014 |
| WO | WO-2014189974 | 11/2014 |
| WO | WO-2014191994 | 12/2014 |
| WO | WO-2014194178 | 12/2014 |
| WO | WO-2014201384 | 12/2014 |
| WO | WO-2014201452 | 12/2014 |
| WO | WO-2014205064 | 12/2014 |
| WO | WO-2014207699 | 12/2014 |
| WO | WO-2014210124 | 12/2014 |
| WO | WO-2014210299 | 12/2014 |
| WO | WO-2015009503 | 1/2015 |
| WO | WO-2015020971 | 2/2015 |
| WO | WO-2015028986 | 3/2015 |
| WO | WO-2015051430 | 4/2015 |
| WO | WO-2015052663 | 4/2015 |
| WO | WO-2015057407 | 4/2015 |
| WO | WO-2015057735 | 4/2015 |
| WO | WO-2015057995 | 4/2015 |
| WO | WO-2015061378 | 4/2015 |
| WO | WO-2015061431 | 4/2015 |
| WO | WO-2015061463 | 4/2015 |
| WO | WO-2015061533 | 4/2015 |
| WO | WO-2015075128 | 5/2015 |
| WO | WO-2015081775 | 6/2015 |
| WO | WO-2015089334 | 6/2015 |
| WO | WO-2015092554 | 6/2015 |
| WO | WO-2015120122 | 8/2015 |
| WO | WO-2015125024 | 8/2015 |
| WO | WO-2015127264 | 8/2015 |
| WO | WO-2015127283 | 8/2015 |
| WO | WO-2015128739 | 9/2015 |
| WO | WO-2015128741 | 9/2015 |
| WO | WO-2015128747 | 9/2015 |
| WO | WO-2015132667 | 9/2015 |
| WO | WO-2015132668 | 9/2015 |
| WO | WO-2015135050 | 9/2015 |
| WO | WO-2015142648 | 9/2015 |
| WO | WO-2015142834 | 9/2015 |
| WO | WO-2015148241 | 10/2015 |
| WO | 2015179181 | 11/2015 |
| WO | WO-2015171190 | 11/2015 |
| WO | WO-2015171743 | 11/2015 |
| WO | WO-2015184452 | 12/2015 |
| WO | WO-2015191604 | 12/2015 |
| WO | WO-2015191839 | 12/2015 |
| WO | WO-2015195823 | 12/2015 |
| WO | WO-2016011185 | 1/2016 |
| WO | WO-2016020918 | 2/2016 |
| WO | WO-2016027272 | 2/2016 |
| WO | WO-2016059533 | 4/2016 |
| WO | WO-2016065158 | 4/2016 |
| WO | WO-2016073741 | 5/2016 |
| WO | WO-2016083551 | 6/2016 |
| WO | WO-2016093877 | 6/2016 |
| WO | WO-2016097337 | 6/2016 |
| WO | WO-2016108181 | 7/2016 |
| WO | 2016133950 | 8/2016 |
| WO | 2016150806 | 9/2016 |
| WO | 2016201024 | 12/2016 |
| WO | 2016209970 | 12/2016 |
| WO | 2017011697 | 1/2017 |
| WO | 2017062640 | 4/2017 |
| WO | 2017096157 | 6/2017 |
| WO | 2017100927 | 6/2017 |
| WO | 2017101232 | 6/2017 |
| WO | 2017117388 | 7/2017 |
| WO | 2017127939 | 8/2017 |
| WO | 2017136596 | 8/2017 |
| WO | 2017196511 | 11/2017 |
| WO | 2017196909 | 11/2017 |
| WO | 2017196977 | 11/2017 |
| WO | 2017197064 | 11/2017 |
| WO | 2017218671 | 12/2017 |
| WO | 2018017886 | 1/2018 |
| WO | 2018029680 | 2/2018 |

OTHER PUBLICATIONS

Bernard et al., "Aortic Valve Area Evolution After Percutaneous Aortic Valvuloplasty," European Heart Journal, Jul. 1990, vol. 11 (2), pp. 98-107.

BlueCross BlueShield of Northern Carolina Corporate Medical Policy "Balloon valvuloplasty, Percutaneous", (Jun. 1994).

Cimino et al., "Physics of Ultrasonic Surgery Using Tissue Fragmentation: Part I and Part II", Ultrasound in Medicine and Biologyl, Jun. 1996, vol. 22 (1), pp. 89-100, and pp. 101-117.

Cimino, "Ultrasonic Surgery: Power Quantification and Efficiency Optimization", Aesthetic Surgery Journal, Feb. 2001, pp. 233-241.

Cowell et al., "A Randomized Trial of Intensive Lipid-Lowering Therapy in Calcific Aortic Stenosis," NEJM, Jun. 2005, vol. 352 (23), pp. 2389-2397.

De Korte et al., "Characterization of Plaque Components and Vulnerability with Intravascular Ultrasound Elastography", Phys. Med. Biol., Feb. 2000, vol. 45, pp. 1465-1475.

European Search Report dated Mar. 13, 2015 for European Application. No. 05853460.3.

Feldman, "Restenosis Following Successful Balloon Valvuloplasty: Bone Formation in Aortic Valve Leaflets", Cathet Cardiovasc Diagn, May 1993, vol. 29 (1), pp. 1-7.

Fitzgerald et al., "Intravascular Sonotherapy Decreased Neointimal Hyperplasia After Stent Implantation in Swine", Circulation, Feb. 2001, vol. 103, pp. 1828-1831.

Freeman et al., "Ultrasonic Aortic Valve Decalcification: Serial Doppler Echocardiographic Follow Up", J Am Coll Cardiol., Sep. 1990, vol. 16 (3), pp. 623-630.

(56) References Cited

OTHER PUBLICATIONS

Greenleaf et al., "Selected Methods for Imaging Elastic Properties of Biological Tissues", Annu. Rev. Biomed. Eng., Apr. 2003, vol. 5, pp. 57-78.
Gunn et al., "New Developments in Therapeutic Ultrasound-Assisted Coronary Angioplasty", Curr Interv Cardiol Rep., Dec. 1990, vol. 1 (4), pp. 281-290.
Guzman et al., "Bioeffects Caused by Changes in Acoustic Cavitation Bubble Density and Cell Concentration: A Unified Explanation Based on Cell-to-Bubble Ratio and Blast Radius", Ultrasound in Med. & Biol., Mar. 2003, vol. 29 (8), pp. 1211-1222.
Hallgrimsson et al., "Chronic Non-Rheumatic Aortic Valvular Disease: a Population Study Based on Autopsies", J Chronic Dis., Jun. 1979, vol. 32 (5), pp. 355-363.
Isner et al., "Contrasting Histoarchitecture of Calcified Leaflets from Stenotic Bicuspid Versus Stenotic Tricuspid Aortic Valves", J Am Coll Cardiol., Apr. 1990, vol. 15 (5), p. 1104-1108.
Lung et al., "A Prospective Survey of Patients with Valvular Heart Disease in Europe: The Euro Heart Survey on Valvular Heart Disease", Euro Heart Journal, Mar. 2003, vol. 24, pp. 1231-1243.
McBride et al. "Aortic Valve Decalcification", J Thorac Cardiovas-Surg, Jul. 1990, vol. 100, pp. 36-42.
Miller et al., "Lysis and Sonoporation of Epidermoid and Phagocytic Monolayer Cells by Diagnostic Ultrasound Activation of Contrast Agent Gas Bodies", Ultrasound in Med. & Biol., May 2007, vol. 27 (8), pp. 1107-1113.
Mohler, "Mechanisms of Aortic Valve Calcificaion", Am J Cardiol, Dec. 2004, vol. 94 (11), pp. 1396-1402.
Otto et al., "Three-Year Outcome After Balloon Aortic Valvuloplasty. Insights into Prognosis of Valvular Aortic Stenosis", Circulation, Feb. 1994, vol. 89, pp. 642-650.
Passik et al., "Temporal Changes in the Causes of Aortic Stenosis: A Surgical Pathologic Study of 646 Cases", Mayo Clin Proc, Feb. 1987, vol. 62, pp. 19-123.
Quaden et al., "Percutaneous Aortic Valve Replacement: Resection Before Implantation", Eur J Cardiothorac Surg, Jan. 2005, vol. 27, pp. 836-840.
Riebman et al., "New Concepts in the Management of Patients with Aortic Valve Disease", Abstract, Valvular Heart Disease, JACC, Mar. 2004, p. 34A.
Rosenschein et al., "Percutaneous Transluminal Therapy of Occluded Saphenous Vein Grafts" Circulation, Jan. 1999, vol. 99, pp. 26-29.
Sakata et al., "Percutaneous Balloon Aortic Valvuloplasty: Antegrade Transseptal vs. Conventional Retrograde Transarterial Approach", Catheter Cardiovasc Interv., Mar. 2005, vol. 64 (3), pp. 314-321.
Sasaki et al., "Scanning Electron Microscopy and Fourier Transformed Infrared Spectroscopy Analysis of Bone Removal Using Er:YAG and CO2 Lasers", J Periodontol., Jun. 2002, vol. 73 (6), pp. 643-652.
Search Report and Written Opinion dated Dec. 10, 2012 for PCT Application No. PCT/US2012/043636.
Search Report and Written Opinion dated Dec. 6, 2016 for PCT Application No. PCT/US2016/047831.
Search Report and Written Opinion dated Jan. 30, 2013 PCT Application No. PCT/US2012/061215.
Search Report and Written Opinion dated Jan. 30, 2013 PCT Application No. PCT/US2012/061219.
Search Report and Written Opinion dated Mar. 2, 2015 for PCT Application No. PCT/US2014/029549.
Search Report and Written Opinion dated May 1, 2012 for PCT Application No. PCT/US2011/065627.
Search Report and Written Opinion dated May 22, 2007 for PCT Application No. PCT/US2005/044543.
Search Report and Written Opinion dated Oct. 20, 2014 for PCT Application No. PCT/US2014/038849.
Search Report and Written Opinion dated Sep. 4, 2014 for PCT Application No. PCT/US2014/014704.
The CoreValve System Medtronic, 2012, 4 Pages.
Van Den Brand et al., "Histological Changes in the Aortic Valve after Balloon Dilation: Evidence for a Delayed Healing Process", Br Heart J, Jun. 1992, vol. 67, pp. 445-459.
Verdaadadonk et al., "The Mechanism of Action of the Ultrasonic Tissue Resectors Disclosed Using High-Speed and Thermal Imaging Techniques", SPIE, Jan. 1999, vol. 3594, pp. 221-231.
Voelker et al., "Inoperative Valvuloplasty in Calcific Aortic Stenosis: a Study Comparing the Mechanism of a Novel Expandable Device with Conventional Balloon Dilation", Am Heart J., Nov. 1991, vol. 122 (5), pp. 1327-1333.
Waller et al., "Catheter Balloon Valvuloplasty of Stenotic Aortic Valves. Part II: Balloon Valvuloplasty During Life Subsequent Tissue Examination", Clin Cardiol., Nov. 1991, vol. 14 (11), pp. 924-930.
Wang, "Balloon Aortic Valvuloplasty", Prog Cardiovasc Dis., Jul.-Aug. 1997, vol. 40 (1), pp. 27-36.
Wilson et al., "Elastography—The movement Begins", Phys. Med. Biol., Jun. 2000, vol. 45, pp. 1409-1421.
Yock et al., "Catheter-Based Ultrasound Thrombolysis", Circulation, Mar. 1997, vol. 95 (6), pp. 1411-1416.
International Search Report and Written Opinion dated Sep. 11, 2018 for PCT Application No. PCT/US2018/038841, 15 pages.
International Search Report and Written Opinion dated Sep. 4, 2018 for PCT Application No. PCT/US2018/027966, 17 pages.
International Search Report and Written Opinion dated Jul. 11, 2018 for PCT Application No. PCT/US2018/027990, 15 pages.
International Search Report and Written Opinion dated Jun. 28, 2018 for PCT Application No. PCT/US2018/027983, 15 pages.
International Search Report and Written Opinion dated Aug. 3, 2018 for PCT Application No. PCT/U.S. Pat. No. 2018035086, 15 pages.
International Search Report and Written Opinion dated Aug. 9, 2018 for PCT Application No. PCT/US2018/035081, 11 pages.
International Search Report and Written Opinion dated Sep. 11, 2018 for PCT Application No. PCT/US2018/038847, 18 pages.
Notice on Reexamination, CN Application No. 201780026591.1, dated Sep. 1, 2022.

* cited by examiner

PROSTHETIC HEART VALVE DEVICES WITH TETHERED ANCHORS AND ASSOCIATED SYSTEMS AND METHODS

CROSS-REFERENCE TO RELATED APPLICATIONS

The present application is a continuation of U.S. patent application Ser. No. 16/293,557, filed Mar. 15, 2019, which is a continuation of U.S. patent application Ser. No. 15/489,889, filed Apr. 17, 2017, which claims priority to U.S. Provisional Patent Application No. 62/329,400, filed Apr. 29, 2016, each of which is incorporated by reference herein in its entirety.

TECHNICAL FIELD

The present technology relates generally to prosthetic heart valve devices. In particular, various embodiments of the present technology are related to prosthetic mitral valve devices with tethered anchors and associated methods and systems.

BACKGROUND

The mitral valve acts as a check valve to prevent flow of oxygenated blood back into the left atrium during systole, i.e., when the left ventricle contracts. This allows oxygenated blood to pump into the aorta through the aortic valve. Regurgitation of the mitral valve can significantly decrease the pumping efficiency of the heart and thereby increase the risk of severe, progressive heart failure. Mitral valve regurgitation can be characterized by retrograde flow from the left ventricle of a heart through an incompetent mitral valve into the left atrium. Mitral valve regurgitation can result from a number of mechanical defects. For example, leaflets, chordae tendineae coupled to the leaflets, and/or the papillary muscles of the mitral valve may be damaged or otherwise dysfunctional. In at least some instances, the mitral valve annulus itself may be damaged, dilated, or weakened such that the mitral valve does not close adequately during systole.

One mechanism for treating mitral valve regurgitation is mitral valve replacement. Percutaneous mitral valve replacement is significantly more challenging than aortic valve replacement because the native mitral valve and surrounding structures pose unique anatomical obstacles. Unlike the relatively symmetric and uniform native aortic valve, the mitral valve annulus has a non-circular, D-shape or kidney-like shape, with a non-planar saddle-like geometry. Such complexity makes it difficult to design a mitral valve prosthesis that conforms adequately to the mitral annulus to prevent leakage and backflow. For example, gaps between the prosthesis and the native tissue allow backflow of blood through the gaps from the left ventricle to the left atrium. As a result, cylindrical valve prostheses may leave gaps in commissural regions of the native valve that potentially result in perivalvular leaks in those regions.

In addition to its irregular, unpredictable shape, which changes size over the course of each heartbeat, the mitral valve annulus also lacks a significant amount of radial support from surrounding tissue. The aortic valve, for example, is completely surrounded by fibro-elastic tissue that provides the native structural support to anchor a prosthetic valve. The inner wall of the native mitral valve, however, is bound by a thin vessel wall separating the mitral valve annulus from the inferior portion of the aortic outflow tract. As a result, significant radial forces on the mitral annulus, such as those exerted by expanding stent prostheses, could cause collapse of the inferior portion of the aortic tract. Further, since the chordae tendineae extend from the papillary muscles to the underside of the leaflets, deploying a valve prosthesis on the ventricular side of the native mitral annulus is challenging. Thus, prosthetic mitral valves must accommodate the difficult anatomy of the mitral valve and surrounding structures.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

DETAILED DESCRIPTION

The present technology is generally directed to prosthetic heart valve devices with tethered anchors and associated systems and methods. Specific details of several embodiments of the present technology are described herein with reference to FIGS. 1A-3C. Although many of the embodiments are described with respect to devices, systems, and methods for prosthetic heart valve devices for replacement of a native mitral valve, other applications and other embodiments in addition to those described herein are within the scope of the present technology. For example, at least some embodiments of the present technology may be useful for replacement of other valves, such as the tricuspid valve or the aortic valve. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

With regard to the terms "distal" and "proximal" within this description, unless otherwise specified, the terms can reference relative positions of portions of a prosthetic valve device and/or an associated delivery device with reference to an operator and/or a location in the vasculature or heart. For example, in referring to a delivery catheter suitable to deliver and position various prosthetic valve devices described herein, "proximal" can refer to a position closer to the operator of the device or an incision into the vasculature, and "distal" can refer to a position that is more distant from the operator of the device or further from the incision along the vasculature (e.g., the end of the catheter). With respect to a prosthetic heart valve device, the terms "proximal" and "distal" can refer to the location of portions of the device with respect to the direction of blood flow. For example, proximal can refer to an upstream position or a position of blood inflow, and distal can refer to a downstream position or a position of blood outflow.

Figure 1A:
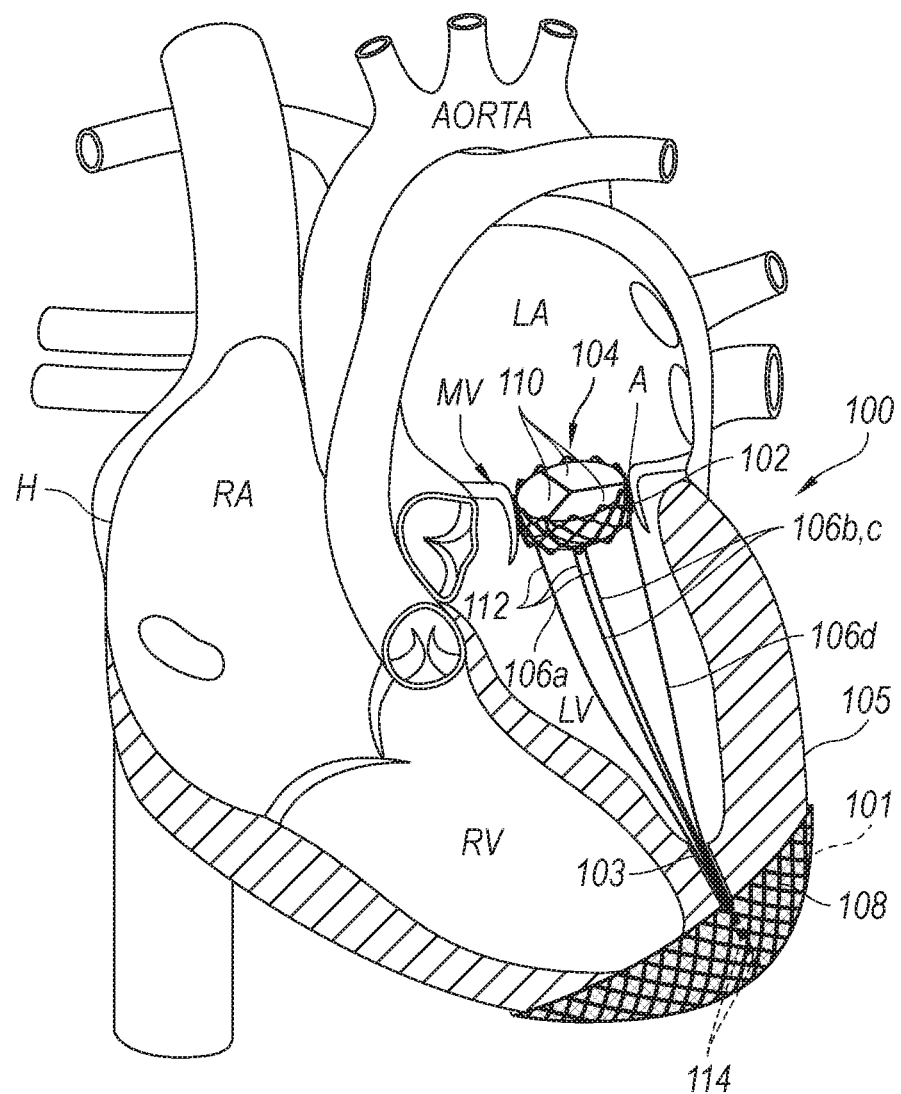
FIG. 1A is a partial cross-sectional side view of a heart valve device positioned in a heart in accordance with an embodiment of the present technology.
Figure 1B:
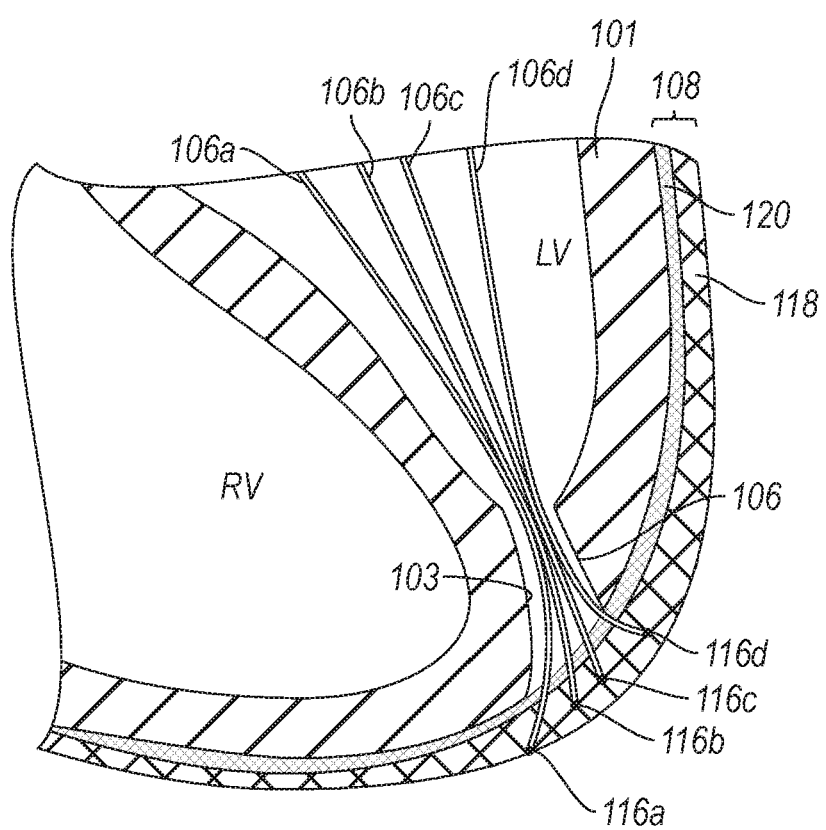
FIG. 1B is an enlarged cross-sectional view of a portion of the heart valve device of FIG. 1A.

FIG. 1A is a partial cross-sectional side view of a heart valve device 100 ("device 100") positioned in a heart H in accordance with an embodiment of the present technology, and FIG. 1B is an enlarged cross-sectional view of a portion of the device 100. As shown in FIG. 1A, the device 100 includes a valve support 102 for carrying a prosthetic valve 104 and a plurality of elongated flexible members (identified individually as first through fourth elongated flexible members 106a-106d, respectively; referred to collectively as elongated flexible members 106). The elongated flexible members 106 extend from the valve support 102 in a distal or ventricular direction. The device 100 further includes an anchor 108 coupled to the valve support 102 via the elongated flexible members 106. The anchor 108 can be shaped and sized to wrap around or otherwise at least substantially conform to an exterior area of an apical portion 101 of the heart H. The valve support 102 can be implanted at or proximate to an annulus A of a native mitral valve MV of the heart H, and the elongated flexible members 106 can extend from the valve support 102 in a ventricular direction through an opening 103 in the apical portion 101 of the heart wall 105 to the anchor 108. The elongated flexible members 106 can tether the valve support 102 to the anchor 108 such that the anchor 108 opposes movement of the valve support 102 in an atrial or proximal direction. Accordingly, the tethered anchor 108 inhibits retrograde migration of the valve support 102.

The device 100 can be compressible from an expanded or deployed state (shown in FIG. 1A) to low-profile, delivery state such that the device 100 can be delivered to a target site (e.g., the mitral valve MV). As discussed in further detail below, when in the low-profile delivery state, the device 100 can be constrained within a delivery catheter (not shown) that can, for example, trans-apically, transfemorally, or trans-septally deliver the device 100 to the target site. At the target site, the valve support 102 can deploy from the delivery catheter and transform to the larger, expanded state such that the valve support 102 engages native tissue at the target site, such as the native annulus A of the mitral valve MV, the leaflets L, and/or other tissue at the mitral valve MV. In various embodiments, the valve support 102 can self-expand to the expanded state. In other embodiments, the valve support 102 may be expanded using a balloon catheter or other stent-expansion devices. In other embodiments, the valve support 102 may be mechanically expandable.

The valve support 102 can be made from a stent or other type of frame that can carry the prosthetic valve 104. For example, valve support 102 can be made from a resilient biocompatible material that moves from the low-profile delivery state to the expanded state, such as stainless steel, platinum, nickel cobalt or cobalt chromium alloys (e.g., MP35N), nickel titanium alloys (e.g., Nitinol), and/or other suitable frame materials for carrying prosthetic valves. When the valve support 102 is made from superelastic shape memory materials, such as Nitinol, the valve support 102 can be collapsed into a very low profile delivery configuration suitable for delivery through the vasculature via a catheter (not shown), and self-expand when unconstrained from the catheter to a deployed configuration suitably sized to replace the target valve. The valve support can be a braided or woven frame, a laser-cut frame made from a metal tube, and/or other suitable stent structures.

The prosthetic valve 104 can include two, three, or more leaflets 110 that are arranged in a bicuspid, tricuspid, or other suitable valve configuration and attached to the valve support 102 using sutures, glue, and/or other suitable attachment mechanisms for joining the prosthetic valve 104 to the valve support 102. The leaflets 110 may be formed of various biocompatible, flexible, and at least substantially impermeable materials. For example, the leaflets 110 can be made from polytetrafluoroethylene (PTFE), polyethylene terephthalate, pyrolytic carbon, biologic tissue (e.g., pericardial tissue or xenograft valve tissue such as porcine heart tissue or bovine pericardium), and/or other biocompatible materials. During valve operation in a mitral application, the leaflets 110 move from a closed position in which blood flow is blocked from passing through the valve support 102 from the left ventricle to the left atrium and an open position in which blood flows through the valve support 102 in a downstream direction from the left atrium to the left ventricle. The valve support 102 can serve as a scaffold having radial rigidity to maintain a circular or other desired cross-sectional shape of the prosthetic valve 104 to ensure that the leaflets 110 coapt or otherwise seal when the device 100 is subject to external radial pressure (e.g., during systole). Suitable valve supports 102 and prosthetic valves 104 are described in, for example, U.S. patent application Ser. No. 13/664,652 to Duffy et al., filed Oct. 31, 2012; U.S. Pat. No. 8,323,336 to Hill et al., filed Apr. 23, 2009; PCT Patent Application No. PCT/US2012/043636 to Gifford et al., filed Jun. 21, 2012; PCT Patent Application No. PCT/US2012/061215 to Morriss et al., filed Oct. 19, 2012; PCT Patent Application No. PCT/US2012/061219 to Morriss et al., filed Oct. 19, 2012; and PCT Patent Application No. PCT/US2014/29549 to Morriss et al., filed Mar. 14, 2014. All of the foregoing applications and patents are incorporated herein by reference in their entireties.

The elongated flexible members 106 can be lines, tethers, chords, and/or other structures for connecting the valve support 102 to the anchor 108. In the embodiment illustrated in FIG. 1A, the device 100 includes four flexible members 106. In other embodiments, the device 100 can include one, two, three, or more than four flexible members 106. Each flexible member 106 shown in FIGS. 1A-1B includes a first end portion 112 attached to the valve support 102 and a second end portion 114 attached to the anchor 108. In other embodiments (note shown), the valve support 102 can be attached to a harness having one or more chords (e.g., three or four chords) that extend from the valve support 102 downwardly into the left ventricle and a single line that attaches the harness to the anchor 108. The first end portions 112 in the illustrated embodiment are independently attached to the valve support 102 at different, spaced apart portions of the valve support 102. For example, the first end portions 112 are spaced apart around the circumference or perimeter of the valve support 102. The first end portions 112 can be attached to a proximal region of the valve support 102 (e.g., near the left atrium LA), a central region of the valve support 102, a distal region of the valve support 102 (e.g., near the left ventricle LV), an outer side of the valve support 102, and/or to an inner side of the valve support 102. The first end portions 112 can be attached to individual struts of the valve support 102, intersections of struts of the valve support 102, a graft material associated with the valve support 102, and/or tether attachment loops or points on the valve support 102. Various attachment mechanisms can be used to attach the first end portions 112 to the valve support 102, such as tying the first end portions 112 to portions of the valve support 102, fastening the first end portions 112 to the valve support 102 using clips, tabs, clamps, and/or other fasteners, and/or gluing the first end portions to portions of the valve support. In further embodiments, the first end portions 112 of the elongated flexible members 106 can be attached to the leaflets 110. For example, the first end portions 112 can be drawn through the leaflets and fastened via sutures, tabs, and/or other suitable fastening mechanisms.

As shown in FIGS. 1A and 1B, the elongated flexible members 106 can extend from the valve support 102, through the left ventricle LV, and through the opening 103 in the heart wall 105 to where the second end portions 114 attach to the anchor 108. The second end portions 114 of the elongated flexible members 106 can be attached to the anchor 108 at a single attachment point on the anchor 108. As shown in FIG. 1B, in other embodiments the individual second end portions 114 of the elongated flexible members 106 can be attached at separate attachment regions (identified as first through fourth attachment regions 116a-116d, respectively; referred to collectively as attachment regions 116) spaced apart from each other on the anchor 108. These separate attachment regions 116 can facilitate distribution of the force applied by each of the elongated flexible members 106 across the anchor 108. The second end portions 114 can be attached to the anchor 108 using fasteners (e.g., clips, tabs, sutures, and/or glue), or the second end portions 114 may themselves be tied at the attachment regions 116.

The elongated flexible members 106 can be made from synthetic or harvested bio-compatible materials. These materials may be selected such that they resist fatigue failure even after high numbers of cycles under which the flexible members 106 undergo relatively high levels of stress experienced during systole. Suitable materials for the elongated flexible members 106 may be elastic or inelastic, and may include biocompatible polymer materials, such as PFTE (polytetrafluoroethylene), polypropylene, ultra-high molecular weight polyethylene, nylon, silk, polyester, PVDF (polyvinylidene fluoride), and/or other suitable biocompatible materials.

In various embodiments, the elongated flexible members 106 may be adjustable in length such that the tension between the valve support 102 and the anchor 108 can be regulated. For example, the second end portions 114 of the elongated flexible members 106 can extend through a fastener at the anchor 108 that only allows movement in one direction (e.g., the proximal or distal direction). An operator can pull or push the second end portions 114 of the individual elongated flexible members 106 (extending through one or more fasteners) until the tension along each of the elongated flexible members 106 has reached a desired degree, and then the single-direction fastener can inhibit retraction of the elongated flexible member 106 toward the valve support 102. In other embodiments, the single-direction fasteners can also or alternatively be attached at the valve support 102. In further embodiments, one end portion of each of the elongated flexible members 106 can remain unattached to either the valve support 102 or the anchor 108, and the end portion can be tied-off or otherwise attached to the valve support 102 or the anchor 108 once the desired length is achieved. In still further embodiments, the elongated flexible members 106 can be non-adjustable and have pre-determined lengths. For example, the predetermined lengths of the elongated flexible members 106 can be determined based on the patient's anatomy before the device implantation procedure. In certain embodiments, the elongated flexible members 106 can each have a length of 2-8 cm. In other embodiments, the elongated flexible members 106 may be shorter than 2 cm or longer than 8 cm depending on the patient's anatomy and/or whether the elongated flexible members 106 are adjustable.

As shown in FIG. 1B, the anchor 108 can be made from a frame 118 and a non-permeable material 120 on the frame 118. In the illustrated embodiment, the non-permeable material 120 is on the interior portion of the frame 118. In other embodiments, however, the non-permeable material 120 can be attached to the exterior of the frame 118 or integrated with the frame 118. In further embodiments, the frame 118 itself can be non-permeable and/or the non-permeable material 120 may be omitted. The frame 118 can be a semi-rigid yet elastic or flexible structure, such as a basket, cage, mesh, mat or other structure made from braided materials, woven materials, linkages, and/or other semi-rigid structures that can maintain a generally convex or cup-like shape, while also being sufficiently flexible to conform to the apical portion 101 of the heart H during the dynamic heart cycle. For example, the frame 118 can be made from a self-expandable material (e.g., Nitinol), carbon and titanium alloys (e.g., Ti-6AL-4V), stainless steel, carbon fiber, and/or other suitable semi-rigid, biocompatible plastic or metal materials. The non-permeable material 120 can be made from a flexible, substantially nonporous material, such as polytetrafluoroethylene (PTFE), expanded polytetrafluoroethylene (ePTFE), polypropylene, polyester, other graft materials, tissue (e.g., synthetic or animal pericardial tissue), and/or polyester.

The anchor 108, when expanded, has a concave interior surface area that curves around and generally conforms to the apical portion 101 of the heart H. In various embodiments, the anchor 108 can be attached to the apical portion 101 of the heart H via self-expansion by wrapping around the exterior surface of the apical portion 101 to secure itself to the heart H. In other embodiments, the anchor 108 may be attached to the apical portion 101 of the heart H via sutures and/or other suitable fasteners that join the anchor 108 to the heart H.

When secured in place, the anchor 108 and tethered connection to the valve support 102 counteract the retrograde forces applied to the valve support 102 during ventricular contraction. This prevents retrograde movement of the valve support 102 to maintain the desired position of the valve support 102 within the mitral valve MV. Because the anchor 108 stabilizes the valve support 102 and counters the force applied to the support 102 during systole, the valve support 102 itself must not include the same level of fixation structures and mechanisms that would be necessary to secure itself to the native annulus A as prosthetic heart valve devices that do not include the elongated flexible members 106 and the anchor 108. For example, the valve support 102 may have relatively small fixation area that contacts the native tissue (e.g., at the annulus A) and, therefore, facilitates the use of a smaller delivery catheter. In certain embodiments, for example, the proximal or superior portion of the valve support 102 does not extend above the native annulus.

The force imparted on the valve support 102 during systole and transferred to the anchor 108 by the elongated flexible members 106 can spread across the surface area of the anchor 108. This is expected to apply a less concentrated force to the anchor 108 and the opposing region of the heart wall 105 than if the elongated flexible members 106 were attached to a smaller fastener at a single point at the apical portion 101 of the heart H near the opening 103 in the heart wall 105. In certain embodiments, for example, the interior surface area of the anchor 108 (i.e., the surface area facing the apical portion 101 of the heart wall 105) can be several times greater than the area of the opening 103 in the heart wall 105 through which the elongated flexible members 106 extend. For example, the opening 103 in the heart wall 105 may be 18 Fr (6 mm in diameter), and the anchor 108 may have dimensions (e.g., an inner diameter or other cross-sectional dimension) corresponding to the dimensions of the apex of the patient's heart, which can vary from about 10 mm to 100 mm in diameter. Accordingly, the interior surface area of the anchor 108 can be two, three, five, ten, twenty, thirty, or more times larger than the opening 103. The anchor 108 is sized and shaped to conform to the three-dimensional curvature of the apex of the heart H such that the anchor 108 provides sufficient surface area to distribute the stresses applied to the anchor 108 by the elongated flexible members 106. Therefore, the anchor 108 can limit the degree of stress applied to the apical region 101 and to the ventricles and avoid damage to the opposing tissue of the heart wall 105.

The anchor 108 can also serve as a sealing mechanism that seals the opening 103 between in the heart wall 105 through which the elongated flexible members 106 extend. When the device 100 is implanted trans-apically, the opening 103 must be formed in the apical region 101 to deliver the device 100 to the mitral valve MV. Accordingly, the anchor 108 can be a substitute for purse string sutures or other closure mechanisms that are typically used to close the opening formed during trans-apical implantation procedures. In other embodiments, the opening 103 in the apical region 101 can be sutured or otherwise closed, and the anchor 108 can cover the closed opening 103.

In addition, the large basket-like structure of the anchor 108 supports the apical portion 101 of the heart and may thus inhibit expansion of the left ventricle LV. Patients that undergo mitral valve replacement often have progressive heart disease, which typically dilates (e.g., enlarges and/or lengthens) the left ventricle LV of the heart and expands the mitral valve MV such that the native leaflets no longer coapt. By wrapping around the apical portion 101 of the heart H and being semi-rigid, the anchor 108 also supports the apical portion 101 in its current state to reduce the likelihood of further expansion and maintain the ventricular structure. In further embodiments, the anchor 108 is configured to contract around the apical portion 101 to limit dilation and potentially decrease the size of the left ventricle LV.

Figure 2A:
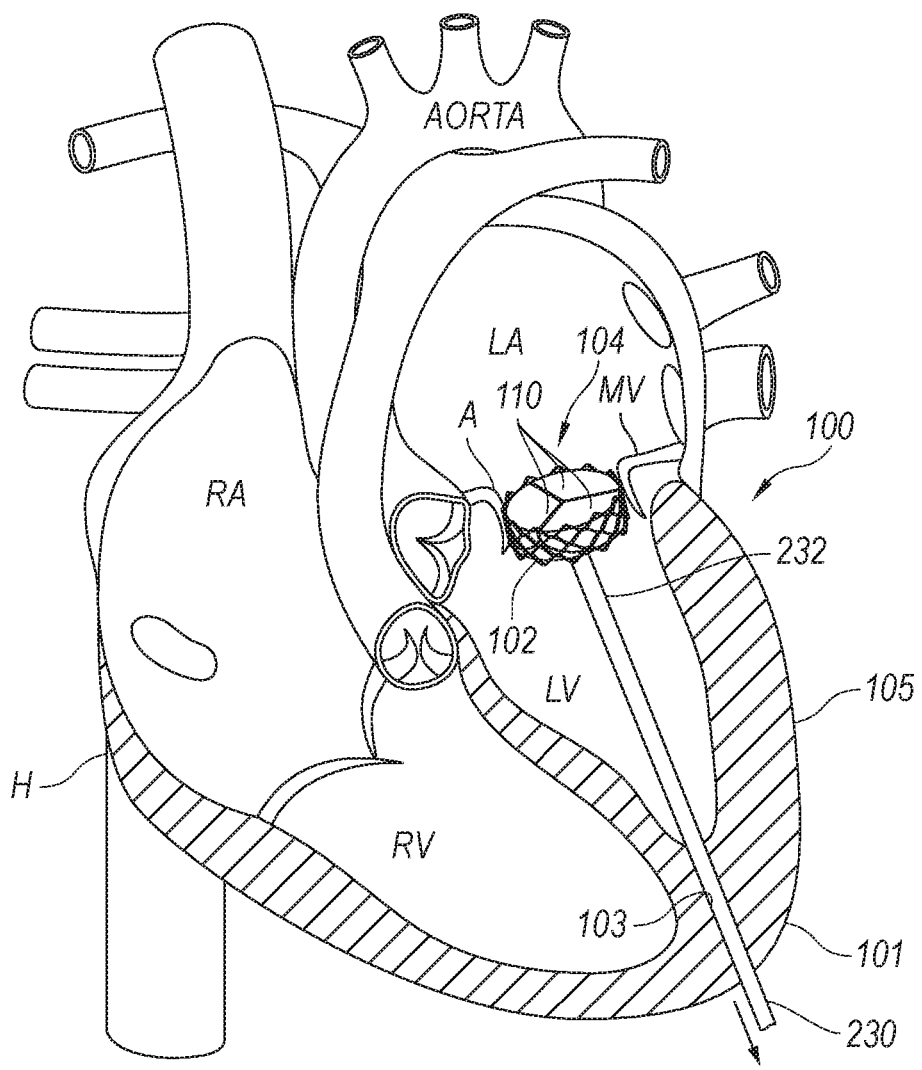
FIGS. 2A-2C are partial cross-sectional side views illustrating stages of a trans-apical implantation procedure of a heart valve device in accordance with an embodiment of the present technology.
Figure 2B:
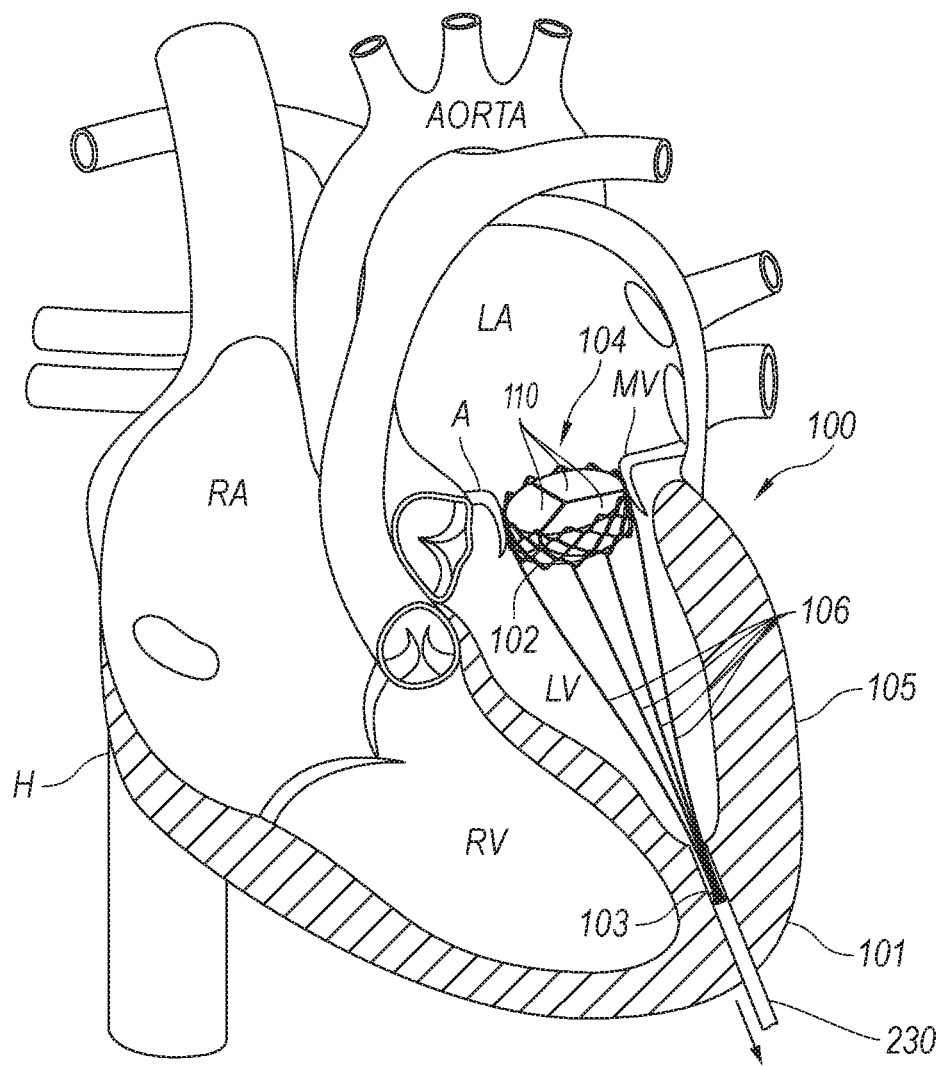
Figure 2C:
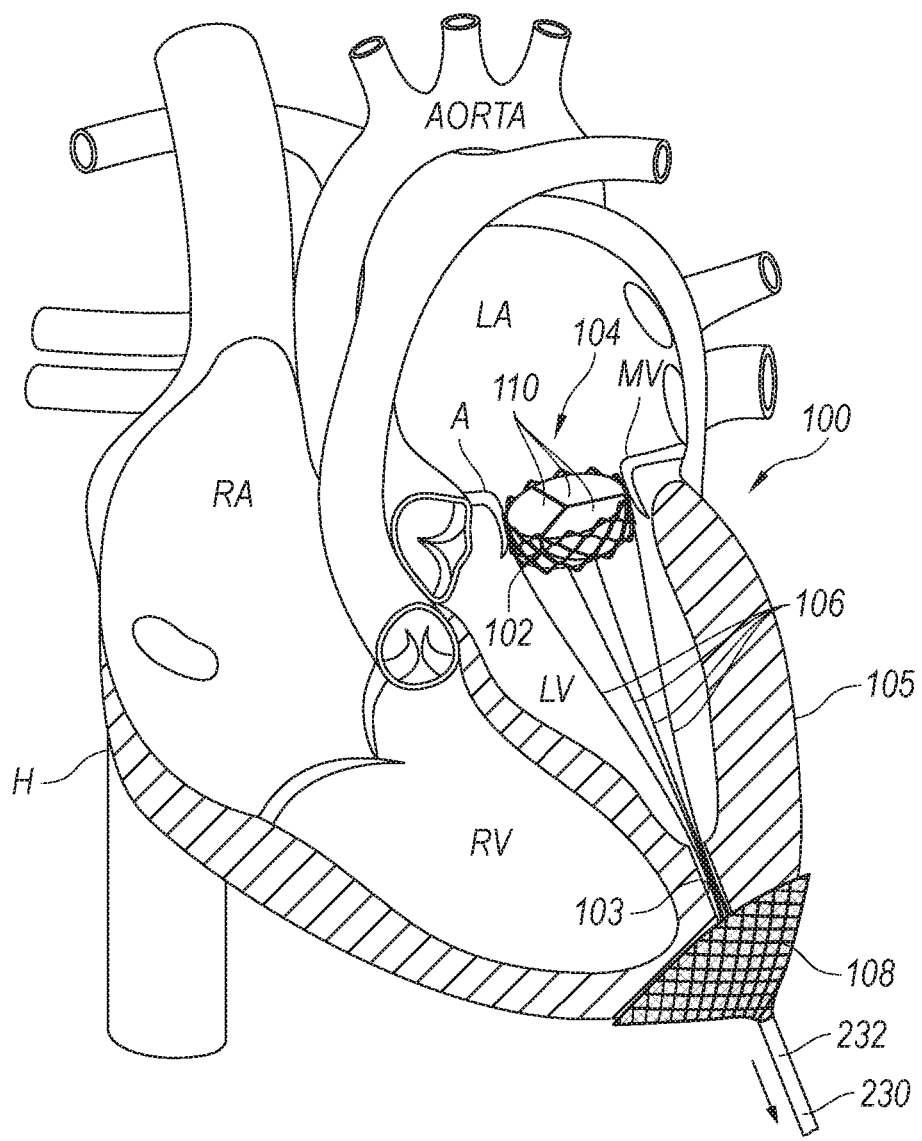

FIGS. 2A-2C are side views illustrating stages of a trans-apical implantation procedure of the device 100 of FIGS. 1A and 1B in accordance with an embodiment of the present technology. The device 100 can be deployed using a delivery catheter 230, which can be controlled by an operator using a control apparatus (e.g., a handle; not shown) at a proximal portion (not shown) of the delivery catheter 230 outside of the patient. During a trans-apical delivery, the device 100 is compressed to a low-profile delivery state within a distal portion 232 of the delivery catheter 230, and the distal portion 232 delivery catheter 230 is inserted through the opening 103 into the left ventricle LV. As shown in FIG. 2A, once the distal end of the delivery catheter 230 is at the target site proximate to the annulus A of the mitral valve MV, the valve support 102 is released from the distal portion 232 of the delivery catheter 230 and expanded to a deployed state such that the valve support 102 contacts the native annulus A and/or surrounding tissue. The valve support 102 can self-expand to the deployed state or may be expanded using a balloon catheter and/or other type of expansion device.

After the valve support 102 is secured in position at the mitral valve MV, the delivery catheter 230 is retracted in a proximal direction (i.e., toward an operator, in a ventricular direction away from the mitral valve MV). As shown in FIG. 2B, as the delivery catheter 230 is withdrawn, the elongated flexible members 106 are deployed from the distal portion 232 of the delivery catheter 230 and through the opening 103 in the heart wall 105.

Upon exiting the opening 103, the anchor 108 is released from the delivery catheter 230 and expanded around the apical portion 101 of the heart. In various embodiments, the anchor 108 may self-expand around the exterior heart wall 105 to attach to the apical portion 101 of the heart. In other embodiments, the anchor 108 may be sutured or otherwise attached to the exterior heart wall 105. In embodiments where the anchor 108 is non-permeable, the anchor 108 can also seal the opening 103 (FIGS. 2A and 2B) in the heart wall 105 through which the device 100 was delivered to the mitral valve MV. In other embodiments, the opening 103 may be sutured or otherwise closed before or after deployment of the anchor 108. In embodiments where the elongated flexible members 106 are adjustable in length, the length of the flexible members 106 are adjusted, if needed, as the anchor 108 is deployed and/or after the anchor 108 has been deployed such that the flexible members 106 have the desired tautness between the valve support 102 and the anchor 108. After deployment, the anchor 108 inhibits retrograde movement or other migration of the valve support 102 by opposing forces applied to the valve support 102 during systole. The large, cup-like anchor 108 is expected to spread the forces applied to the anchor 108 by the elongated support members 106 across a relatively large surface area compared to a single-point tether connection, thereby reducing the force per area applied to the heart wall 105. Further, the conformal, cup-like anchor 108 may also support the apical portion 101 of the heart to stabilize and inhibit ventricular dilation as explained above.

Figure 3B:
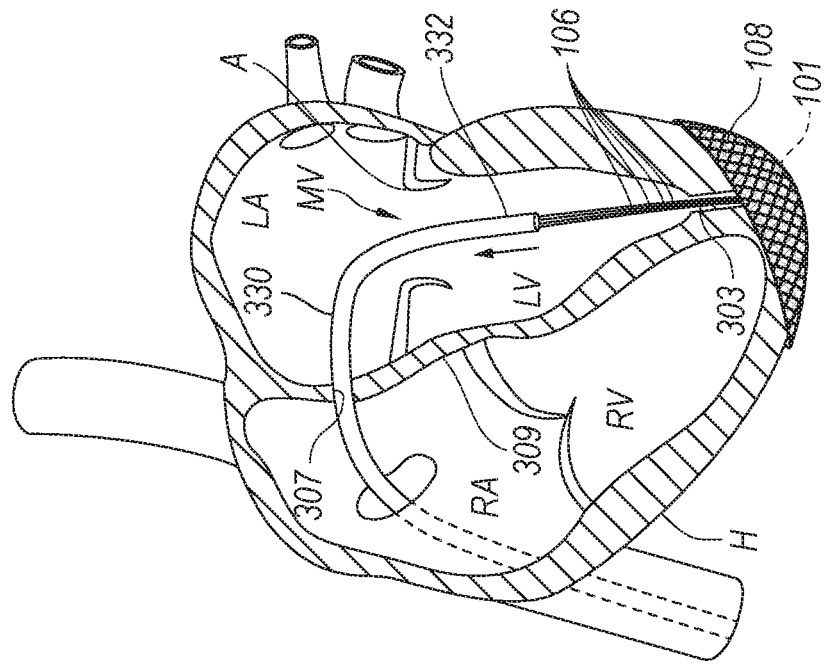
FIGS. 3A-3C are partial cross-sectional side views illustrating stages of a trans-septal implantation procedure of a heart valve device in accordance with an embodiment of the present technology.
Figure 3A:
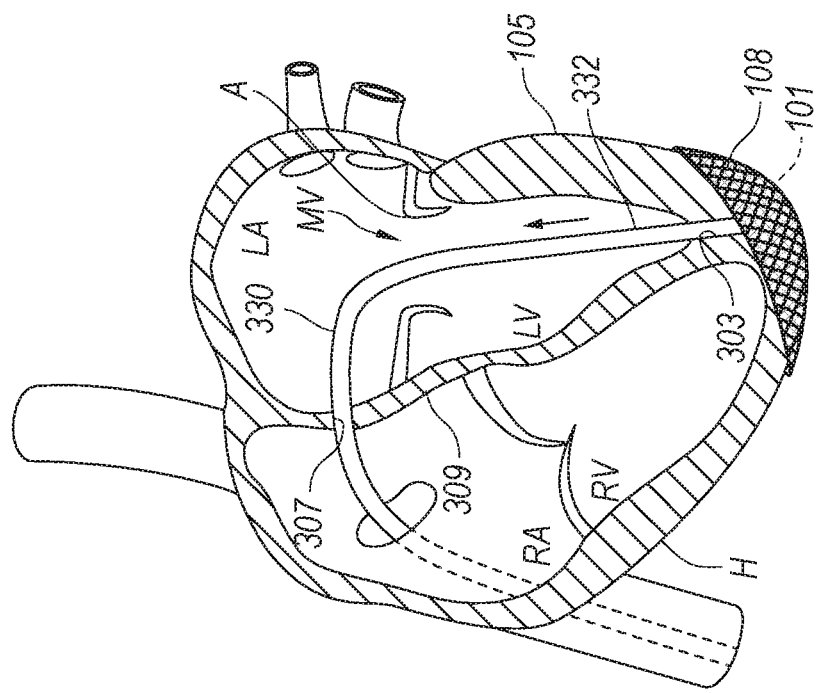
Figure 3C:
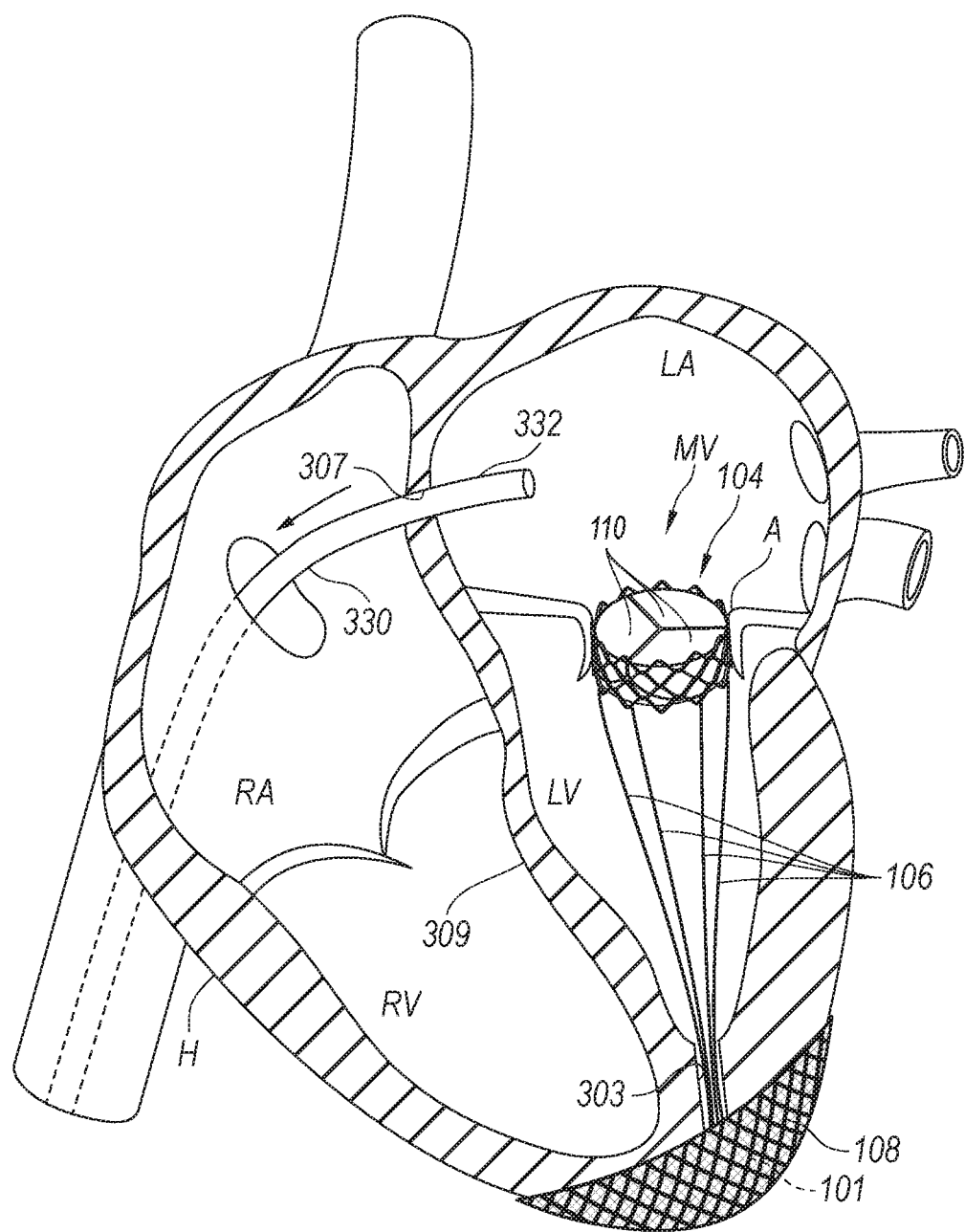

FIGS. 3A-3C are side views illustrating stages of a trans-septal implantation procedure of the device 100 of FIGS. 1A and 1B in accordance with an embodiment of the present technology. Similar to the trans-apical delivery procedure discussed above with reference to FIGS. 2A-2C, the device 100 can be trans-septally deployed from a distal portion 332 of a delivery catheter 330 that is controlled using a control apparatus (e.g., a handle; not shown) at a proximal portion (not shown) of the delivery catheter 330 (outside of the patient). However, unlike the trans-apical delivery procedure, the trans-septal delivery can be performed intravascularly and the deployment of the device 100 occurs in generally the opposite order as the order of deployment during the trans-apical procedure. In this embodiment, the delivery catheter 330 is intravascularly delivered to the right atrium of the heart (e.g., via the aorta or the superior vena cava). A septal opening 307 is then formed in a septal wall 309 between the right and left atria such that the distal portion 332 of the delivery catheter 330 can be positioned in the left atrium.

As shown in FIG. 3A, the distal portion 332 of the delivery catheter 330 is passed through the mitral valve MV, into the left ventricle LV, and through an opening 303 formed in the apical portion 101 of the heart wall 105. The opening 303 in the apical portion 101 of the heart wall 105 and the septal opening 307 can be formed using various hole-forming devices (e.g., coring needles) coupled to the delivery catheter 330 and/or a separate device that is advanced before the distal portion 332 of the delivery catheter 330. Once the distal portion 332 of the delivery catheter 330 is positioned at the exterior of the heart wall 105, the anchor 108 can self-expand or otherwise deploy from the distal portion 332 around an exterior wall of the apical portion 101 of the heart. In this embodiment, the opening 303 may be smaller than the opening 103 (FIGS. 2A-2C) for trans-apical deployment because only the anchor 108 needs to be deployed through the opening 303, not the valve support 102 and the valve 104, which may have a larger cross-sectional dimension than the anchor 108. The deployed anchor 108 can seal the opening 303 created to deploy the anchor 108, or the opening 303 may be sutured or otherwise closed upon retraction of the delivery catheter 330 through the opening 303.

As the delivery catheter 330 retracts through the opening 303 into the left ventricle LV, the elongated flexible members 106 are released from the catheter 330 (FIG. 3B). At the target site proximate to the mitral valve MV, the valve support 102 is deployed from distal portion 332 of the delivery catheter 330 and expanded to an expanded or deployed state such that the valve support 102 is placed in apposition with the native annulus A and/or surrounding tissue of the mitral valve MV (FIG. 3C). In certain embodiments, the elongated flexible members 106 can be adjusted to provide a desired degree of tension between the anchor 108 and the valve support 102 such that the anchor 108 can inhibit retrograde movement of the valve support 102 during systole. After the device 100 is fully deployed, the delivery catheter 330 can retract into the left atrium LA and back through the opening 307, which can be sutured or otherwise closed before the delivery catheter 330 is withdrawn from the body.

ADDITIONAL EXAMPLES

1. A heart valve device for implantation in a native mitral valve of a heart, the heart valve device comprising:
   a valve support for carrying a prosthetic valve, wherein the valve support is configured to be implanted at an annulus of the native mitral valve;
   at least one elongated flexible member extending from the valve support in a ventricular direction; and
   an anchor coupled to the valve support via the elongated flexible member, wherein the anchor is shaped to wrap around an exterior area of an apical portion of the heart, and wherein the anchor is configured to inhibit retrograde migration of the valve support.

2. The heart valve device of example 1 wherein:
   the elongated flexible member is configured to extend through an opening in the apical portion of the heart to connect to the anchor; and
   the anchor comprises a material configured to cover and seal the opening in the apical portion of the heart.

3. The heart valve device of example 1 or 2 wherein the elongated flexible member comprises a first elongated flexible member and a second elongated flexible member, and wherein the first elongated flexible member connects to a first region of the anchor and the second elongated flexible member connects to a second region of the anchor spaced apart, the first region being spaced apart from the second region.

4. The heart valve device of any one of examples 1-3 wherein the elongated flexible member is a tether that restricts movement between the valve support and the anchor.

5. The heart valve device of any one of examples 1-4 wherein the anchor comprises a semi-rigid frame and a non-permeable material on the frame.

6. The heart valve device of any one of examples 1-5 wherein the anchor comprises a self-expandable frame having a conformal concave shape, the anchor being configured to self-expand to attach to the apical portion of the heart.

7. The heart valve device of any one of examples 1-6 wherein the anchor is sized and shaped to contract around the apical portion of the heart to lessen left ventricle dilation.

8. The heart valve device of any one of examples 1-7 wherein the anchor comprises a mesh basket configured to conform to the apical portion of the heart.

9. The heart valve device of any one of examples 1-8 wherein:
   the valve support comprises a frame portion that supports the prosthetic valve; and
   the elongated flexible member connects to the frame portion.

10. The heart valve device of any one of examples 1-8 wherein:
    the valve support comprises a frame portion that supports the prosthetic valve;
    the prosthetic valve comprises a plurality of leaflets; and
    the elongated flexible member connects to one of the leaflets of the prosthetic valve.

11. The heart valve device of any one of examples 1-10 wherein the elongated flexible member is adjustable in length.

12. The heart valve device of example 1 wherein:
    the valve support comprises a frame portion;
    the elongated flexible member is one of a plurality of elongated flexible members connected to the frame portion at a plurality of spaced apart connection sites around a circumference of the frame portion;
    the plurality of elongated flexible members are sized to extend from the frame portion through an opening in the apical portion of the heart to connect to the anchor; and
    the anchor comprises a self-expandable material having a concave shape corresponding to the apical portion of the heart and configured to cover and seal the opening in the apical portion of the heart.

13. A heart valve device for implantation in a native valve of a heart, the heart valve device comprising:
    a valve support configured to support a prosthetic valve;
    an anchor having a surface area configured to attach and conform to an exterior portion of the heart downstream of the native valve; and
    a plurality of elongated flexible members connecting the valve support to the anchor.

14. The heart valve device of example 13 wherein:
    the valve support is sized and shaped to be implanted in a native annulus of a native mitral valve; and
    the anchor is configured to attach to an apical portion of the heart proximate to a left ventricle of the heart.

15. The heart valve device of example 13 or 14 wherein the anchor comprises a self-expandable material, and wherein the anchor self-expands to a convex shape.

16. The heart valve device of any one of examples 13-15 wherein the elongated flexible members are flexible lines connected between the valve support and the anchor.

17. The heart valve device of any one of examples 13-16 wherein the anchor comprises a woven basket having a cup-shape configured to grip the apical portion of the heart.

18. A heart valve device for implantation in a native valve of a heart, the heart valve device comprising:
- a valve support for carrying a prosthetic valve, wherein the annulus is configured to be implanted at an annulus of the native valve;
- an anchor comprising a mesh structure having a concave shape when expanded, wherein the mesh structure is configured to conform to an exterior portion of an apical region of the heart; and
- at least one elongated flexible member connecting the valve support to the anchor.

19. The heart valve device of example 18 wherein the mesh structure is made of nitinol.

20. A method of implanting a heart valve device in a native valve of a heart, the method comprising:
- delivering, via a delivery catheter, the heart valve device to a chamber of the heart proximate to a native annulus of the native valve;
- deploying a valve support from the delivery catheter into fixation against the native annulus;
- deploying at least one elongated flexible member from the delivery catheter, wherein the elongated flexible member is connected to the valve support;
- extending the elongated flexible member through an opening in a portion of the heart downstream of the native valve; and
- deploying an anchor to conform around an exterior portion of the heart downstream of the native valve, wherein the anchor is configured to seal the opening in the heart and inhibit retrograde migration of the valve support.

21 The method of example 20 wherein deploying the valve support comprises affixing the valve support to the native annulus such that a superior portion of the valve support does not extend above the native annulus.

22. The method of example 20 or 21 wherein deploying the anchor comprises allowing the anchor to self-expand to a concave shape conforming to an exterior apical portion of the heart.

23. The method of any one of examples 20-22 wherein:
- delivering the heart valve device to the chamber of the heart comprises trans-apically delivering the delivery catheter to a left ventricle of the heart;
- deploying the valve support comprises affixing the valve support against the native annulus of a mitral valve of the heart; and
- extending the elongated flexible member through the opening in the heart comprises extending the elongated flexible member through the same opening in the left ventricle of the heart used to deliver the delivery catheter to the left ventricle.

24 The method of any one of examples 20-22 wherein:
- delivering the heart valve device to the chamber of the heart comprises trans-septally delivering the delivery catheter to a left ventricle of the heart; and
- deploying the anchor occurs before deploying the valve support such that the delivery catheter is drawn in an upstream direction to expose the elongated flexible member and deploy the valve support.

25. The method of any one of examples 20-24, further comprising adjusting a length of the elongated flexible member such that the elongated flexible member is taut between the valve support and the anchor.

26 The method of any one of examples 20-25, further comprising supporting the exterior portion of the heart with the anchor to inhibit dilation of the exterior portion within the anchor.

27. A method of implanting a heart valve device in a native mitral valve of a heart, the method comprising:
- delivering a delivery catheter across a septal wall of the heart into a chamber of the heart, wherein the delivery catheter contains a heart valve device;
- forming an opening in an apical portion of the heart proximate to a left ventricle of the heart;
- deploying, from the delivery catheter, an anchor at an exterior portion of the apical portion of the native mitral valve;
- deploying at least one elongated flexible member from the delivery catheter, wherein the elongated flexible member extends from the anchor through the opening in the heart; and
- deploying, from the delivery catheter, a valve support into fixation against a native annulus of the native mitral valve, wherein elongated flexible member extends between the valve support and the anchor, and the anchor is configured to inhibit retrograde migration of the valve support.

CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

I claim:

1. A heart valve device for implantation in a native mitral valve of a heart, the heart valve device comprising:
   a valve support for carrying a prosthetic valve, wherein the valve support is configured to be implanted at an annulus of the native mitral valve;
   at least one elongated flexible member extending from the valve support in a ventricular direction and configured to extend through an opening in a left ventricle of an apical portion of the heart; and
   an anchor coupled to the valve support via the at least one elongated flexible member, wherein the anchor is sized and shaped such that when deployed the anchor is sized and shaped to wrap around an exterior area of an apical portion of the heart to inhibit expansion of the apical portion of the left ventricle.

2. The heart valve device of claim 1, wherein the anchor comprises a self-expandable frame configured to expand to a concave shape when deployed such that the frame conforms to the exterior area during dynamic heart cycling.

3. The heart valve device of claim 1 wherein the anchor comprises a material configured to cover and seal the opening in the apical portion of the heart.

4. The heart valve device of claim 1 wherein the at least one elongated flexible member comprises a first elongated flexible member and a second elongated flexible member, and wherein the first elongated flexible member connects to a first region of the anchor and the second elongated flexible member connects to a second region of the anchor, the first region being spaced apart from the second region.

5. The heart valve device of claim 1 wherein the anchor comprises a frame and a non-permeable material coupled to the frame.

6. The heart valve device of claim 1 wherein the at least one elongated flexible member is adjustable in length.

7. The heart valve device of claim 1 wherein:
   the valve support comprises a frame portion;
   the at least one elongated flexible member comprises a plurality of elongated flexible members connected to the frame portion at a plurality of spaced apart connection sites around a circumference of the frame portion;
   the plurality of elongated flexible members are sized to extend from the frame portion through the opening in the apical portion of the heart to connect to the anchor; and
   the anchor comprises a self-expandable material having a concave shape corresponding to the apical portion of the heart and configured to cover and seal the opening in the apical portion of the heart.

8. The heart valve prosthesis of claim 1, wherein the anchor is sized and shaped such that the anchor when deployed the anchor is disposed opposite left and right ventricles of the heart.

9. The heart valve prosthesis of claim 1, wherein an interior surface area of the anchor is at least 850 mm$^2$.

10. A heart valve device for implantation in a native mitral valve of a heart, the heart valve device comprising:
    a valve support for carrying a prosthetic valve, wherein the valve support is configured to be implanted at an annulus of the native mitral valve;
    at least one elongated flexible member extending from the valve support in a ventricular direction and configured to extend through an opening in a left ventricle of an apical portion of the heart; and
    an anchor coupled to the valve support via the at least one elongated flexible member, wherein the anchor is configured to be deployed outside of the heart over the opening, wherein the anchor is configured such that when deployed the anchor contracts around the apical portion of the heart to limit dilation of the left ventricle.

11. The heart valve device of claim 10, wherein the anchor comprises a self-expandable frame configured to expand to a concave shape when deployed.

12. The heart valve device of claim 10 wherein the anchor comprises a material configured to cover and seal the opening in the apical portion of the heart.

13. The heart valve device of claim 10 wherein the at least one elongated flexible member comprises a first elongated flexible member and a second elongated flexible member, and wherein the first elongated flexible member connects to a first region of the anchor and the second elongated flexible member connects to a second region of the anchor, the first region being spaced apart from the second region.

14. The heart valve device of claim 10 wherein the anchor comprises a frame and a non-permeable material coupled to the frame.

15. The heart valve device of claim 10 wherein the at least one elongated flexible member is adjustable in length.

16. The heart valve device of claim 10 wherein:
    the valve support comprises a frame portion;
    the at least one elongated flexible member comprises a plurality of elongated flexible members connected to the frame portion at a plurality of spaced apart connection sites around a circumference of the frame portion;
    the plurality of elongated flexible members are sized to extend from the frame portion through the opening in the apical portion of the heart to connect to the anchor; and
    the anchor comprises a self-expandable material having a concave shape corresponding to the apical portion of the heart and configured to cover and seal the opening in the apical portion of the heart.

17. A heart valve device for implantation in a native mitral valve of a heart, the heart valve device comprising:
    a valve support for carrying a prosthetic valve, wherein the valve support is configured to be implanted at an annulus of the native mitral valve;
    a plurality of separate elongated flexible members including respective first ends coupled to the valve support extending from the valve support in a ventricular direction including at least a first elongated flexible member and a second elongated flexible member, wherein the first and second elongated flexible members are separate from each other, the plurality of elongated flexible members being configured to extend through an opening in an apical portion of the heart; and
    an anchor coupled to the valve support via the elongated flexible member, wherein the anchor is shaped to wrap around an exterior area of an apical portion of the heart, wherein the first elongate flexible member and the second elongate flexible member include separate respective second ends coupled to the anchor at respective first and second regions of the anchor, wherein the first and second regions of the spaced laterally apart from each other.

18. The heart valve device of claim 17, wherein the anchor comprises a self-expandable frame configured to expand to a concave shape when deployed such that the frame conforms to the exterior area.

19. The heart valve device of claim 17 wherein the anchor comprises a material configured to cover and seal the opening in the apical portion of the heart.

20. The heart valve device of claim 17 wherein the at least one elongated flexible member comprises a first elongated flexible member and a second elongated flexible member, and wherein the first elongated flexible member connects to a first region of the anchor and the second elongated flexible member connects to a second region of the anchor, the first region being spaced apart from the second region.

21. The heart valve device of claim 17 wherein the anchor comprises a frame and a non-permeable material coupled to the frame.

22. The heart valve device of claim 17 wherein the at least one elongated flexible member is adjustable in length.

* * * * *